(12) United States Patent
Bamborough et al.

(10) Patent No.: US 9,753,034 B2
(45) Date of Patent: Sep. 5, 2017

(54) PROCESS FOR THE IDENTIFICATION OF A COMPOUND WHICH INHIBITS THE BINDING OF THE FIRST BROMODOMAIN OF EACH OF HUMAN BRD-2, BRD-3, AND BRD-4

(71) Applicant: GLAXOSMITHKLINE LLC, Wilmington, DE (US)

(72) Inventors: Paul Bamborough, Stevenage (GB); Chun-Wa Chung, Stevenage (GB)

(73) Assignee: GLAXOSMITHKLINE LLC, Wilmington, DE (US)

( * ) Notice: Subject to any disclaimer, the term of this patent is extended or adjusted under 35 U.S.C. 154(b) by 0 days.

(21) Appl. No.: 15/157,620

(22) Filed: May 18, 2016

(65) Prior Publication Data
US 2016/0258946 A1 Sep. 8, 2016

Related U.S. Application Data

(62) Division of application No. 13/505,474, filed as application No. PCT/EP2010/066714 on Nov. 3, 2010, now Pat. No. 9,360,482.

(30) Foreign Application Priority Data

Nov. 5, 2009 (GB) .................................. 0919430.9
Feb. 22, 2010 (GB) .................................. 1002974.2

(51) Int. Cl.
| | | |
|---|---|---|
| *G01N 21/64* | (2006.01) | |
| *G01N 33/566* | (2006.01) | |
| *C12N 9/12* | (2006.01) | |
| *G01N 33/68* | (2006.01) | |

(52) U.S. Cl.
CPC ......... *G01N 33/566* (2013.01); *C12N 9/1205* (2013.01); *G01N 33/6803* (2013.01); *G01N 2500/02* (2013.01); *G01N 2500/10* (2013.01)

(58) Field of Classification Search
CPC ............. G01N 33/566; G01N 33/6803; G01N 2500/02; G01N 2500/10; C12N 9/1205
See application file for complete search history.

(56) References Cited

U.S. PATENT DOCUMENTS

| 5,185,331 A | 2/1993 | Freidinger et al. | |
|---|---|---|---|
| 2004/0043378 A1* | 3/2004 | Zhou .................... | A61K 31/198 435/5 |

FOREIGN PATENT DOCUMENTS

| CA | 2710740 | 7/2009 |
|---|---|---|
| EP | 0934940 | 8/1999 |
| GB | 2242134 A | 3/1991 |
| JP | 2008-156311 | 7/2008 |
| WO | WO 2005-044354 | 5/2005 |
| WO | WO 2007/016087 | 2/2007 |
| WO | WO 2007/084625 | 7/2007 |

OTHER PUBLICATIONS

Berge et al., "Pharmaceutical salts", J. Pharm. Sci., 66:1-19, (1977).
Bock, et al., "Cholecystokinin Antagonists. Synthesis and biological evaluation of 4-substituted 4H-[1,2,4]Triazolo[4,3-a][1,4]benzodiazepines", J. Med. Chem., 31(1):176-181 (1988).
(Continued)

*Primary Examiner* — Shafiqul Haq
(74) *Attorney, Agent, or Firm* — Natalie A. Lissy

(57) ABSTRACT

A process for the identification of compounds with a molecular weight in the range 100 to 750 which inhibit the binding of the first and/or second bromodomains of human BRD-2 to 4 to acetylated lysine residues of their physiological partner proteins which comprises selecting those compounds which are able to:
a) form a hydrogen bonding interaction in which the compound accepts a hydrogen bond from the sidechain NH2 group of the asparagine residue found at:

| BRD-2 BD1 | BRD-2 BD2 | BRD-3 BD1 | BRD-3 BD2 | BRD-4 BD1 | BRD-4 BD2 |
|---|---|---|---|---|---|
| ASN156 | ASN429 | ASN116 | ASN391 | ASN140 | ASN433 | or
b) accept a water-mediated hydrogen bond in which the compound accepts a hydrogen bond from a water that is itself hydrogen-bonded to the sidechain hydroxyl of the tyrosine residue found at

| BRD-2 BD1 | BRD-2 BD2 | BRD-3 BD1 | BRD-3 BD2 | BRD-4 BD1 | BRD-4 BD2 |
|---|---|---|---|---|---|
| TYR113 | TYR386 | TYR73 | TYR348 | TYR97 | TYR390 | and
c) which are also able to form a Van der Waals interaction with a lipophilic binding region of a binding pocket such that one or more heavy atoms of the said compounds lie within a 5 Å range of any of the heavy atoms of the following bromodomain residues which define the binding pocket:

| BRD-2 BD1 | BRD-2 BD2 | BRD-3 BD1 | BRD-3 BD2 | BRD-4 BD1 | BRD-4 BD2 |
|---|---|---|---|---|---|
| TRP97 | TRP370 | TRP57 | TRP332 | TRP81 | TRP374 |
| PRO98 | PRO371 | PRO58 | PRO333 | PRO82 | PRO375 |
| ASP161 | ASP434 | ASP121 | GLU396 | ASP145 | GLU438 |
| ILE162 | VAL435 | ILE122 | VAL397 | ILE146 | VAL439 |
| MET165 | MET438 | MET125 | MET400 | MET149 | MET442 | pharmaceutical compositions containing such compounds, and their use in therapy.

8 Claims, 6 Drawing Sheets

(56) References Cited

OTHER PUBLICATIONS

Chen, et al., "N-Alkoxycarbonyl-glutamic and aspartic acids", Int. J. Peptide Protein Res. 40:13-18 (1992).
European Search Report dated Feb. 24, 2016 for application No. EP 15155397.1.
French et al., "*BRD4-NUT* Fusion Oncogene: A Novel Mechanism in Aggressive Carcinoma", Cancer Research, 63:304-307 (2003).
French et al., "Midline Carcinoma of Children and Young Adults With *NUT* Rearrangement", Journal of Clinical Oncology, 22(20):4135-4139 (2004).
French, et al., "BRD-NUT oncoproteins: A family of closely related nuclear proteins that block epithelial differentiation and maintain the growth of carcinoma cells", Oncogene, 27:2237-2242 (2008).
Hargreaves et al, "Control of Inducible Gene Expression by Signal-Dependent Transcriptional Elongation", Cell, 138(1):129-145 (2009).
Hopkins, et al., Ligand efficiency: A useful metric for lead selection: Drug Discovery Today, 9(10):430-431 (2004).
Huang, et al., "Solution structure of the second bromodomain of Brd2 and its specific interaction with acetylated histone tails", BMC Structural Biology, 7(1):57-74 (2007).
Kontoyianni et al., "Theoretical and Practical Considerations in Virtual Screening: A Beaten Field?" Current Medicinal Chemistry, 15:107-116 (2008).
LeRoy et al, "The double bromodomain proteins brd2 and brd3 couple histone acetylation to transcription", Mol. Cell. 30(1):51-60 (2008).
Muegge, et al. "Advances in virtual screening", Drug Discovery Today: Technologies, 3:405-411 (2006).
Nakamura, "Crystal structure of the Human BRD2 Bromodomain: Insights into dimerization and recognition of acetylated histone H4", Journal of Biological Chemistry 282(6):4193-4201 (2007).
Partial European Search Report dated Nov. 4, 2015 for application No. EP 15155397.1.
RCSB Protein Data Bank entry 1X0J deposited Mar. 23, 2005.
RCSB Protein Data Bank entry 2CVQ deposited Jun. 13, 2005.
RCSB Protein Data Bank entry 2DRV deposited Jun. 15, 2006.
RCSB Protein Data Bank entry 2DVQ deposited Aug. 1, 2006.
RCSB Protein Data Bank entry 2DVS deposited Aug. 1, 2006.
RCSB Protein Data Bank entry 2DVV depositedAug. 1, 2006.
RCSB Protein Data Bank entry 2DWW deposited Aug. 21, 2006.
RCSB Protein Data Bank entry 2E3K deposited Nov. 27, 2006.
RCSB Protein Data Bank entry 2NXB deposited Nov. 17, 2006.
RCSB Protein Data Bank entry 2OO1 deposited Jan. 25, 2007.
RCSB Protein Data Bank entry 2OSS deposited Feb. 6, 2007.
RCSB Protein Data Bank entry 2OUO deposited Feb. 12, 2007.
Rishi, et al., "A high-throughput fluorescence-anisotropy screen that identifies small molecule inhibitors of the DNA binding of B-ZIP transcription factors", Analytical Biochemistry, 340:259-271 (2005).
Seifert, et al., "Essential factors for successful virtual screening", Mini-Reviews in Medicinal Chemistry, 7:63-72 (2007).
Thompson, et al., "Thermodynamic analysis of acetylation-dependent Pb1 bromodomain-histone H3 interactions", Analytical Biochemistry, 374:304-312 (2008).
Umehara, "Structural implications for K5/K12-di-acetylated histone H4 recognition by the second bromodomain of BRD2", FEBS Letter, 584(18):3901-3908 (2010).
UniProtKB sequence database entry O60885 (BRD4_HUMAN) Last modified: Jan. 31, 2002.
UniProtKB sequence database entry P25440 (BRD2_HUMAN) Last modified: Jan. 11, 2001.
UniProtKB sequence database entry Q15059 (BRD3_HUMAN) Last modified: Nov. 1, 1996.
You et al., "Interaction of the bovine papillomavirus E2 protein with Brd4 tethers the viral DNA to host mitotic chromosomes", Cell, 117(3):349-60 (2004).

\* cited by examiner

FIG. 1
Sequence alignment of the human BRD-2, BRD-3 and BRD-4 bromodomains

```
BRD-2_D1  58   PANPPPPEVS NPKKPGRVTN QLQYLHKVVM KALWKHQ..F AWPFRQPVDA
BRD-3_D1  18   PVNPPPPEVS NPSKPGRKTN QLQYMQNVVV KTLWKHQ..F AWPFYQPVDA
BRD-4_D1  42   STNPPPPETS NPNKPKRQTN QLQYLLRVVL KTLWKHQ..F AWPFQQPVDA
BRD-2_D2  339  .......... QSSKKGKLSE QLKHCNGILK ELLSKKHAAY AWPFYKPVDA
BRD-3_D2  301  .......... HAGKKGKLSE HLRYCDSILR EMLSKKHAAY AWPFYKPVDA
BRD-4_D2  343  .......... APEKSSKVSE QLKCCSGILK EMFAKKHAAY AWPFYKPVDV
                                                               ab

BRD-2_D1  106  VKLGLPDYHK IIKQPMDMGT IKRRLENNYY WAASECMQDF NTMFTNCYIY
BRD-3_D1  66   IKLNLPDYHK IIKNPMDMGT IKKRLENNYY WSASECMQDF NTMFTNCYIY
BRD-4_D1  90   VKLNLPDYYK IIKTPMDMGT IKRRLENNYY WNAQECIQDF NTMFTNCYIY
BRD-2_D2  379  SALGLHDYHD IIKHPMDLST VKRKMENRDY RDAQEFAADV RLMFSNCYKY
BRD-3_D2  341  EALELHDYHD IIKHPMDLST VKRKMDGREY PDAQGFAADV RLMFSNCYKY
BRD-4_D2  383  EALGLHDYCD IIKHPMDMST IKSKLEAREY RDAQEFGADV RLMFSNCYKY
                     c

BRD-2 D1  156  NKPTDDIVLM AQTLEKIFLQ KVASMPQEEQ ELVVTIPKNS .....
BRD-3 D1  116  NKPTDDIVLM AQALEKIFLQ KVAQMPQEEV ELLPPAPKGK GRK..
BRD-4 D1  140  NKPGDDIVLM AEALEKLFLQ KINELPTEET EIMIVQAKGR GRGRK
BRD-2 D2  429  NPPDHDVVAM ARKLQDVFEF RYAKMPDEPL EPGPLP.... .....
BRD-3 D2  391  NPPDHEVVAM ARKLQDVFEM RFAKMPDEPV EAPALP.... .....
BRD-4 D2  433  NPPDHEVVAM ARKLQDVFEM RFAKMPDEPE EPVVAV.... .....
                       d     ef  g
```

FIG. 2 - Depiction of compound (I) when bound to BRD-2 BD1
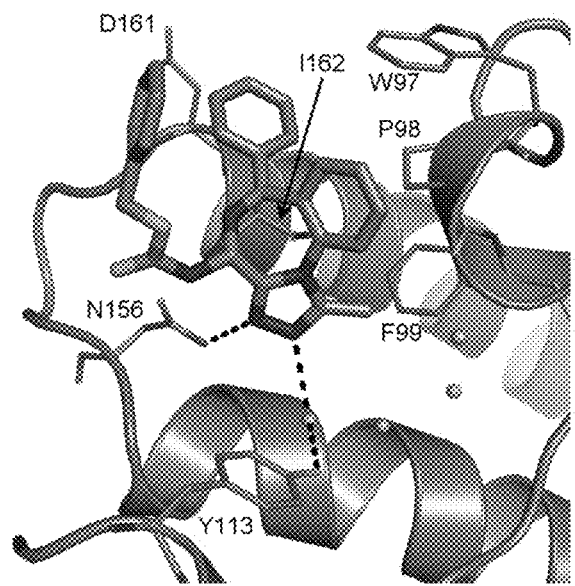
FIG. 3 - Depiction of compound (I) when bound to BRD-4 BD1
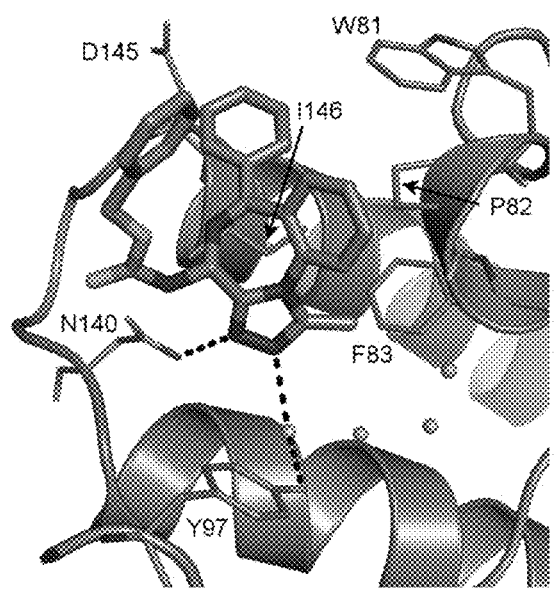

FIG. 4 - Depiction of compound (I) when bound to BRD-4 BD2
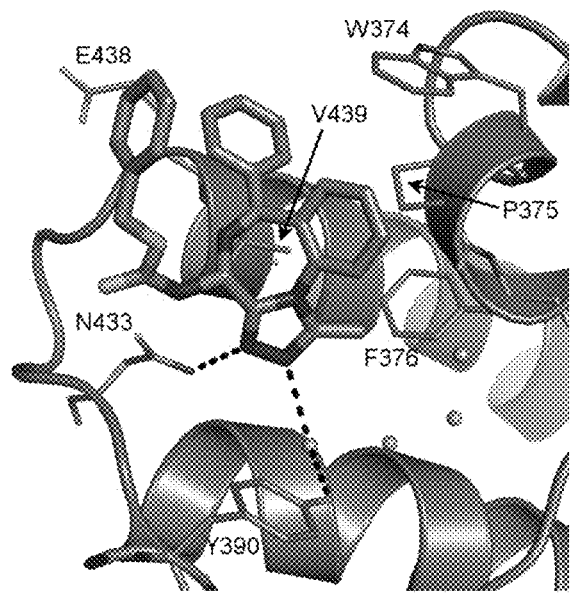
FIG. 5 - Depiction of compound (II) when bound to BRD-2 BD1
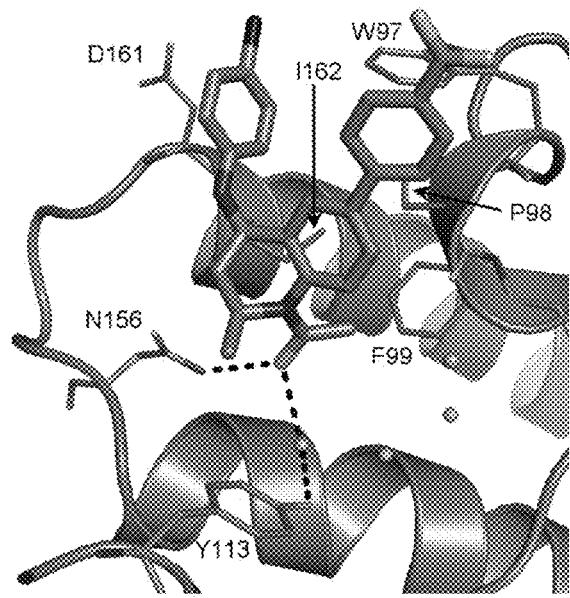

FIG. 6 - Depiction of compound (II) when bound to BRD-2 BD2
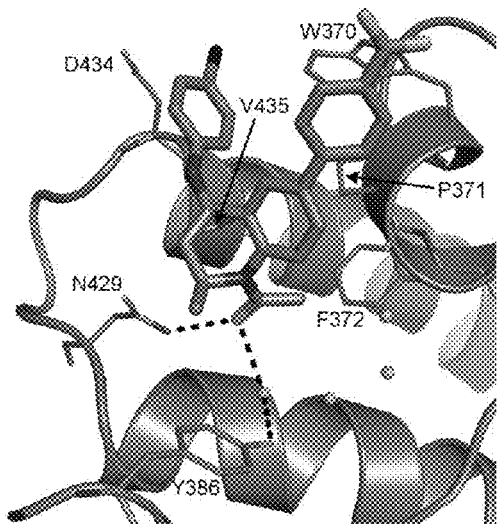
FIG. 7 - Depiction of compound (I) (ball and stick) and compound (II) (stick) when bound to BRD-2 BD1.
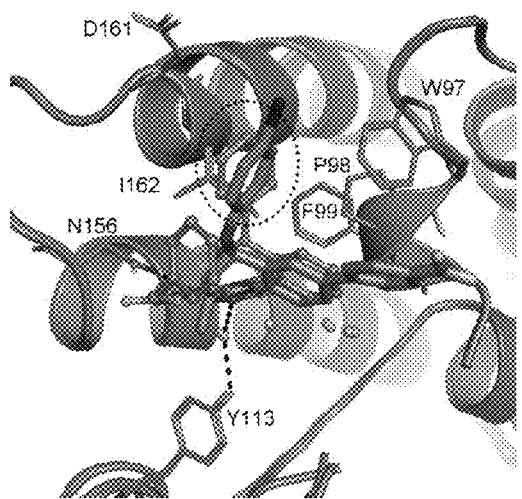

FIG. 8 - Depiction of compound (I) (ball and stick) when bound to BRD-4 BD2, and compound (II) (stick) when bound to BRD-2 BD2.
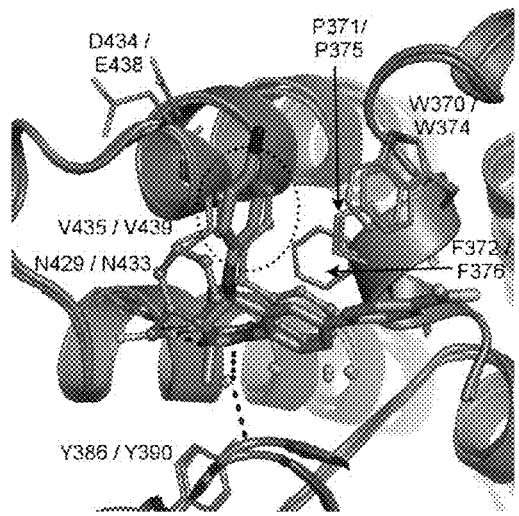
FIG. 9 - Depiction of compound (III) when bound to BRD-2 BD1
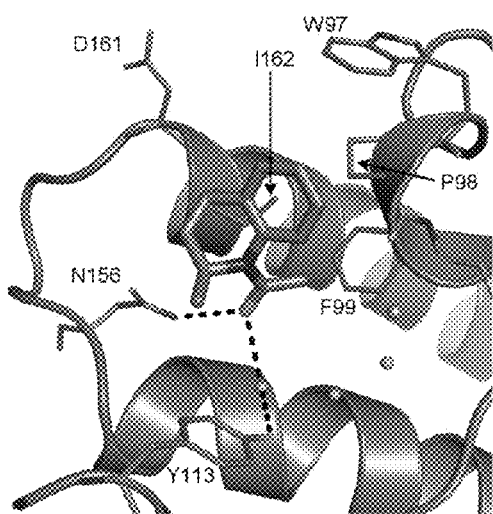

FIG. 10: Depiction of compound (IV) when bound to BRD-2 BD1
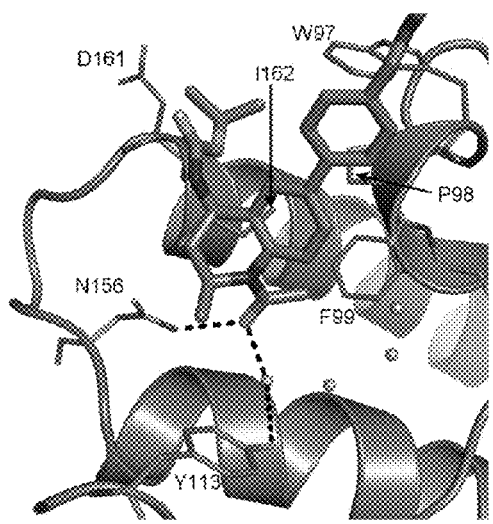
FIG. 11: - Depiction of compound (II) (ball and stick) and compound (IV) (stick) when bound to BRD-2 BD1
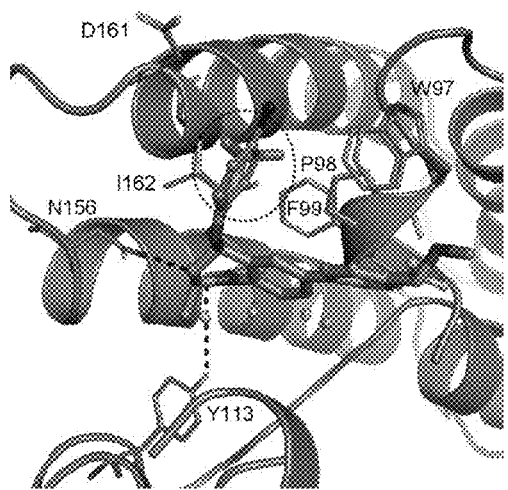

PROCESS FOR THE IDENTIFICATION OF A COMPOUND WHICH INHIBITS THE BINDING OF THE FIRST BROMODOMAIN OF EACH OF HUMAN BRD-2, BRD-3, AND BRD-4

CROSS-REFERENCE TO RELATED APPLICATIONS

This application is a divisional of U.S. application Ser. No. 13/505,474, filed Jun. 20, 2012, which the US National Stage of International Application No. PCT/EP2010/066714, filed Nov. 3, 2010, which International Application claims priority to Great Britain Application No. 0919430.9 filed Nov. 5, 2009, and Great Britain Application No. 1002974.2, filed Feb. 22, 2010, where the contents of each of the preceding are herein incorporated by reference in their entireties.

FIELD OF THE INVENTION

The present invention relates to a process for the identification of small molecules which inhibit the binding of the first and second bromodomains (BD1 and 2, also known as the N- and C-terminal bromodomains) of the human BET family proteins BRD-2 to 4 to acetylated lysine residues of their physiological partner proteins, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine residues commonly but not exclusively in the context of histones. There are a family of around 50 proteins known to contain bromodomains, and they have a range of functions within the cell.

The BET family of bromodomain containing proteins comprises 4 proteins (BRD-2, BRD-3, BRD-4 and BRD-t) which contain tandem bromodomains (BD1 and 2) capable of binding to two acetylated lysine residues in close proximity, increasing the specificity of the interaction. BRD-2 and BRD-3 are reported to associate with histones along actively transcribed genes and may be involved in facilitating transcriptional elongation (Leroy et al, Mol. Cell. 2008 30(1):51-60), while BRD-4 appears to be involved in the recruitment of the pTEF-B complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogensesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Umehara et al have solved the X-ray crystal structure for human BRD-2 BD1 when bound to a histone acetylated lysine residue (Protein crystallographic databank entry 2dvq) and demonstrated that the acetylated lysine residue accepts a hydrogen bond from the sidechain NH2 group of ASN 156 and also accepts a hydrogen bond from a water molecule that is itself hydrogen-bonded to the sidechain hydroxyl of TYR113. They have also predicted the amino acid residues which define the acetyl lysine recognition pocket of the first bromodomain (BD1) of human BRD-2 (JP2008-156311, The Institute of Physical and Chemical Research (RIKEN)). We have now identified small molecules which inhibit the binding of BD1 and 2 of the human BET family proteins BRD-2 to 4 to acetylated lysine residues of their physiological partner proteins. X-ray crystal studies of these molecules when bound to these BET bromodomains have allowed us to retrospectively identify the key binding sites involved in this interaction. This information can be used in the rational drug design of further small molecules which are able to inhibit the binding of the first and/or second bromodomains of human BRD-2 to 4 to acetylated lysine residues of their physiological partner proteins.

SUMMARY OF THE INVENTION

In a first aspect of the present invention, there is provided a process for the identification of small molecules, in particular compounds with a molecular weight in the range 100 to 750, which inhibit the binding of the first and/or second bromodomains of human BRD-2 to 4 to acetylated lysine residues of their physiological partner proteins which comprises selecting those compounds which are able to:
 a) form a hydrogen bonding interaction in which the compound accepts a hydrogen bond from the sidechain NH2 group of the asparagine residue found at:

| BRD-2 BD1 | BRD-2 BD2 | BRD-3 BD1 | BRD-3 BD2 | BRD-4 BD1 | BRD-4 BD2 |
|---|---|---|---|---|---|
| ASN156 | ASN429 | ASN116 | ASN391 | ASN140 | ASN433 | or
b) accept a water-mediated hydrogen bond in which the compound accepts a hydrogen bond from a water that is itself hydrogen-bonded to the sidechain hydroxyl of the tyrosine residue found at

| BRD-2 BD1 | BRD-2 BD2 | BRD-3 BD1 | BRD-3 BD2 | BRD-4 BD1 | BRD-4 BD2 |
|---|---|---|---|---|---|
| TYR113 | TYR386 | TYR73 | TYR348 | TYR97 | TYR390 | and
c) which are also able to form a Van der Waals interaction with a lipophilic binding region of a binding pocket such that one or more heavy atoms of the said compounds lie within a 5 Å range of any of the heavy atoms of the following bromodomain residues which define the binding pocket:

| BRD-2 BD1 | BRD-2 BD2 | BRD-3 BD1 | BRD-3 BD2 | BRD-4 BD1 | BRD-4 BD2 |
|---|---|---|---|---|---|
| TRP97 | TRP370 | TRP57 | TRP332 | TRP81 | TRP374 |
| PRO98 | PRO371 | PRO58 | PRO333 | PRO82 | PRO375 |
| ASP161 | ASP434 | ASP121 | GLU396 | ASP145 | GLU438 |
| ILE162 | VAL435 | ILE122 | VAL397 | ILE146 | VAL439 |
| MET165 | MET438 | MET125 | MET400 | MET149 | MET442 |

From a comparison of the amino acid sequences of the human BET family bromodomains (FIG. 1) a person skilled in the art will appreciate that the residues shown in Table 1 are equivalent. This may also be seen by comparison of the published crystal structures of the BRD-2, BRD-3 and BRD-4 bromodomains, which have all been solved. See Nakamura et al. (J. Biol. Chem. 2007, 282, 4193-4201) for a description of the BRD-2 D1 bromodomain structure, and also protein crystallographic databank entries for BRD-2 D1 (1x0j, 2cvq, 2drv, 2dvs, 2dvq), BRD-2 D2 (2dvv, 2e3k), BRD-3 D1 (2nxb), BRD-3 D2 (2oo1), BRD-4 D1 (2oss) and BRD-4 D2 (2ouo, 2dww).

TABLE 1

|   | BRD-2 BD1 | BRD-2 BD2 | BRD-3 BD1 | BRD-3 BD2 | BRD-4 BD1 | BRD-4 BD2 |
|---|---|---|---|---|---|---|
| a | TRP97 | TRP370 | TRP57 | TRP332 | TRP81 | TRP374 |
| b | PRO98 | PRO371 | PRO58 | PRO333 | PRO82 | PRO375 |
| c | TYR113 | TYR386 | TYR73 | TYR348 | TYR97 | TYR390 |
| d | ASN156 | ASN429 | ASN116 | ASN391 | ASN140 | ASN433 |
| e | ASP161 | ASP434 | ASP121 | GLU396 | ASP145 | GLU438 |
| f | ILE162 | VAL435 | ILE122 | VAL397 | ILE146 | VAL439 |
| g | MET165 | MET438 | MET125 | MET400 | MET149 | MET442 |

In a second aspect of the present invention, there is provided a pharmaceutical composition comprising a compound identified according to the above process, or a pharmaceutically acceptable salt or solvate thereof, and one or more pharmaceutically acceptable carriers, diluents and excipients.

In a third aspect of the present invention, there is provided a compound identified according to the above process, or a pharmaceutically acceptable salt or solvate thereof, for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound identified according to the above process, or a pharmaceutically acceptable salt or solvate thereof.

In a fifth aspect of the present invention, there is provided the use of a compound identified according to the above process, or a pharmaceutically acceptable salt or solvate thereof, in the manufacture of a medicament for the treatment of diseases or conditions for which a bromodomain inhibitor is indicated.

BRIEF DESCRIPTION OF FIGURES

FIG. 1: Sequence alignment of the human BRD-2, BRD-3 and BRD-4 bromodomains. The bromodomains have been extracted from the sequences and aligned to each other. The first residue in each line is numbered according to the entry in the Swissprot sequence database (entries P25440, BRD-2_HUMAN; Q15059, BRD-3_HUMAN; O60885, BRD-4_HUMAN). Key residues are labelled below: a=Trp97, b=Pro98, c=Tyr113, d=Asn156, e=Asp161, f=Ile162, g=Met165 (BRD-2 D1 residues and numbering). As shown, position a is a conserved tryptophan; position b is a conserved proline; position c is a conserved tyrosine; position d is a conserved asparagine; position e is aspartic acid or glutamic acid; position f is isoleucine or valine, and position g is a conserved methionine.

SEQ ID NO: 1 is BRD-2_D1
SEQ ID NO: 2 is BRD-3_D1
SEQ ID NO: 3 is BRD-4_D1
SEQ ID NO: 4 is BRD-2_D2
SEQ ID NO: 5 is BRD-3_D2
SEQ ID NO: 6 is BRD-4_D2

FIG. 2: Depiction of compound (I) when bound to BRD-2 BD1.

FIG. 3: Depiction of compound (I) when bound to BRD-4 BD1.

FIG. 4: Depiction of compound (I) when bound to BRD-4 BD2.

FIG. 5: Depiction of compound (II) when bound to BRD-2 BD1.

FIG. 6: Depiction of compound (II) when bound to BRD-2 BD2.

FIG. 7: Overlay of X-ray crystal structures of compounds (I) (depicted as ball+stick) and (II) (depicted as stick) when bound to BRD-2 BD1 showing the compounds accepting a hydrogen bond from the sidechain NH2 of ASN156 and forming a Van der Waals interaction with a lipophilic region within the binding pocket formed by the residues TRP97, PRO98, ASP161, ILE 162 and MET165 (indicated by a dotted circle).

FIG. 8: Overlay of X-ray crystal structures of compound (I) (depicted as ball+stick) when bound to BRD-4 BD2 and compound (II) (depicted as stick) when bound to BRD-2 BD2 showing the compounds accepting a hydrogen bond from a water molecule that was itself hydrogen-bonded to the sidechain hydroxyl of the tyrosine residue found at position 386 of BRD-2 BD2 or the equivalent 390 position of BRD-4 BD2, and forming a Van der Waals interaction with a lipophilic region within the binding pocket formed by the residues TRP370, PRO371, ASP434, VAL435 and MET438 in BRD-2 BD2 or the equivalent residues TRP374, PRO375, GLU438, VAL439 and MET442 in BRD-4 BD2 (indicated by the dotted circle).

FIG. 9: Depiction of compound (III) when bound to BRD-2 BD1.

FIG. 10: Depiction of compound (IV) when bound to BRD-2 BD1.

FIG. 11: Overlay of X-ray crystal structures of compounds (II) (depicted as ball+stick) and (IV) (depicted as stick) when bound to BRD-2 BD1 showing the compounds accepting a hydrogen bond from the sidechain NH2 of ASN156 and forming a Van der Waals interaction with a lipophilic region within the binding pocket formed by the residues TRP97, PRO98, ASP161, ILE 162 and MET165 (indicated by a dotted circle).

DETAILED DESCRIPTION OF THE INVENTION

A small group of molecules which were shown by classical pharmacological techniques to have an interesting but unexplained anti-inflammatory biological profile were shown through subsequent chemoproetomic studies to bind to the bromodomain regions of the human BET family proteins.

Thus, novel compounds which belong to two different structural classes have been identified which inhibit the binding of the first and/or second bromodomains of human BRD-2 to 4 to acetylated lysine residues of their physiological partner proteins (hereinafter referred to as bromodomain inhibitors). Examples of these bromodomain inhibitors include:

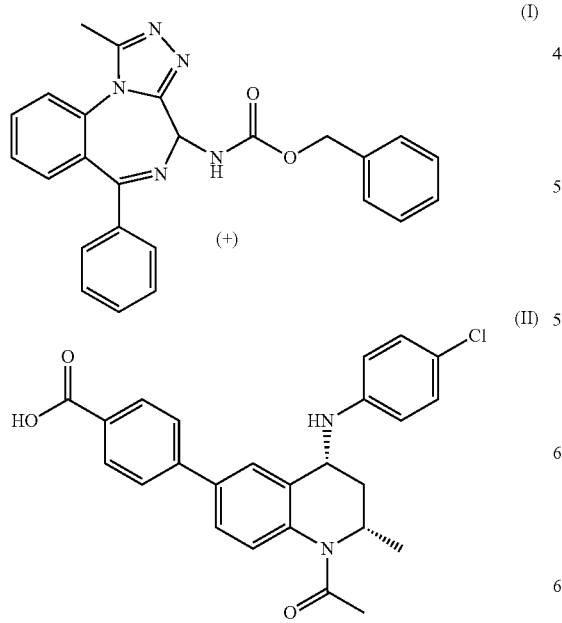

When assessed in a Fluorescence Anisotropy Binding Assay both compounds (I) and (II) above demonstrated a pIC50≥6.0 in each of the BRD-2, BRD-3 and BRD-4 assays.

Analysis of X-ray crystal structures of these bromodomain inhibitors when bound to these BET bromodomains have allowed us to identify the key binding sites involved in this interaction.

In particular. X-ray crystal structures were obtained for compound (I) when bound to BRD-2 BD1, BRD-4 BD1 and BRD-4 BD2, and for compound (II) when bound to BRD-2 BD1 and 2. These are given in each of FIGS. 2 to 6 below.

Comparison of these crystal structures indicated that the structurally unrelated compounds (I) and (II) interact with the key acetylated lysine binding pocket of BRD-2 and 4 in the same way, mimicking the hydrogen-bonding network normally made by the acetylated lysine moiety of histone peptides within this pocket. One interaction was with a sidechain NH2 group of an asparagine residue. Compounds (I) and (II) also interacted with a sidechain hydroxyl of a tyrosine residue via an intermediate water molecule. For example, both compounds (I) and (II) accepted a hydrogen bond from the sidechain NH2 group of the asparagine residue found at the 156 position in BRD-2 BD 1 (see FIGS. 2, 5 and 7). Both compounds (I) and (II) also accepted a hydrogen bond from a water molecule that was itself hydrogen-bonded to the sidechain hydroxyl of the tyrosine residue found at the 390 position of BRD-4 BD2 and the equivalent 386 position of BRD-2 BD2 (see FIGS. 4, 6 and 8).

Further comparison between the different crystal structures obtained led to the identification of a third conserved interaction between the structurally unrelated compounds (I) and (II) and the human proteins BRD-2 and 4. Compounds (I) and (II) were each found to interact with a further binding pocket formed partly by residues of the ZA loop of the bromodomain protein, and partly by residues found at the N-terminal end of the 60 C helix (see Nakamura et al., J. Biol. Chem. 2007, 282, 4193-4201 for definitions). The identity of these residues in each bromodomain are as listed in Table 2.

TABLE 2

| Residues corresponding to the binding pocket | | | | | |
|---|---|---|---|---|---|
| BRD-2 BD1 | BRD-2 BD2 | BRD-3 BD1 | BRD-3 BD2 | BRD-4 BD1 | BRD-4 BD2 |
| TRP97 | TRP370 | TRP57 | TRP332 | TRP81 | TRP374 |
| PRO98 | PRO371 | PRO58 | PRO333 | PRO82 | PRO375 |
| ASP161 | ASP434 | ASP121 | GLU396 | ASP145 | GLU438 |
| ILE162 | VAL435 | ILE122 | VAL397 | ILE146 | VAL439 |
| MET165 | MET438 | MET125 | MET400 | MET149 | MET442 |

For example, both compounds (I) and (II) formed a Van der Waals interaction with a lipophilic region within this binding pocket wherein one or more heavy atoms of the compound lay within a 5 Å range of any of the heavy atoms of the bromodomain residues TRP97, PRO98, ASP161, ILE 162 or MET165 of BRD-2 BD1 (see FIG. 7).

In particular, both compounds (I) and (II) formed a Van der Waals interaction with a lipophilic region within this binding pocket wherein one or more heavy atoms of the compound lay within 7.5 Å of at least one heavy atom of each of PRO98, ASP161 and ILE162 of BRD-2 BD1 (see FIG. 7).

It was noteworthy that this interaction was not observed in the crystal structure of the histone acetylated lysine residue when bound to human BRD-2 BD1. However, surprisingly, interaction with this further binding pocket appears to be of particular importance in conferring activity. Compound (III) set out below shows a marked reduction in pIC50 when assessed in the Fluorescence Anisotropy Binding Assay for the binding of BRD-2 to 4 when compared with compound (II).

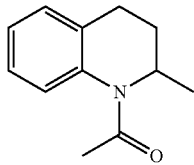
(III)

When assessed in a Fluorescence Anisotropy Binding Assay compound (III) above demonstrated a pIC50≤4.3 in each of the BRD-2, BRD-3 and BRD-4 assays. % Inhibition at 200 µM compound concentration of 34%, 46% and 45% was seen in the BRD-2 to 4 assays respectively, indicating that binding was occurring but at a low level. This is in contrast to compound (II) which demonstrated a pIC50≥6.5 in each of the BRD-2, BRD-3 and BRD-4 assays.

The crystal structure of compound (III) bound to BRD-2 BD1 indicates that the compound accepts a hydrogen bond from the sidechain NH2 group of the asparagine residue found at the 156 position in BRD-2 BD 1. Compound (III) also accepts a hydrogen bond from a water that is itself hydrogen-bonded to the sidechain hydroxyl of the tyrosine residue found at the 113 position in BRD-2 BD1. However, there is no interaction with the binding pocket containing the residues tryptophan, proline, asparagine, isoleucine and methionine (see FIG. 9). Addition of the pendant 4-chloroaniline group, as seen in compound (II), allows interaction with the binding pocket, in addition to the acetylated lysine binding pocket as shown in FIGS. 5 and 7.

Compound (IV) is a further novel bromodomain inhibitor, which when assessed in a Fluorescence Anisotropy Binding Assay demonstrated a pIC50>6.0 in each of the BRD-2, BRD-3 and BRD-4 assays.

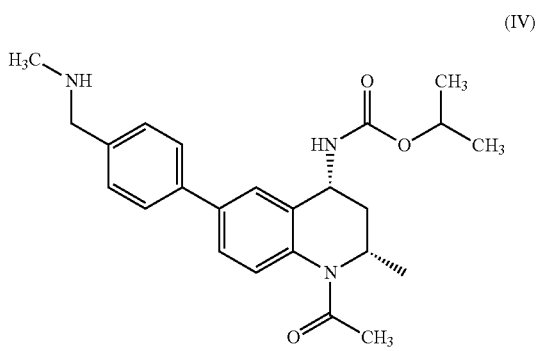 [SMILES: CNCc1ccc(-c2ccc3c(c2)[C@H](NC(=O)OC(C)C)C[C@H](C)N3C(C)=O)cc1]
(IV)

The crystal structure of compound (IV) when bound to BRD-2 BD1 indicates that, like each of the compounds (I) to (III), the compound accepts a hydrogen bond from the sidechain NH2 group of the asparagine residue found at the 156 position in BRD-2 BD1 and also accepts a hydrogen bond from a water that is itself hydrogen-bonded to the sidechain hydroxyl of the tyrosine residue found at the 113 position in BRD-2 BD1 (see FIG. 10).

Further comparison of the X-ray crystal structures of compounds (II) and (IV) when bound to BRD-2 BD1 shows that the key Van der Waals interaction with a lipophilic region within the binding pocket defined by the residues set out in Table 2 was conserved even though the 4-chloroaniline substituent had been replaced with an isopropyl carbamate moiety (see FIG. 11).

From a comparison of the amino acid sequences of the human BET family bromodomains (FIG. 1) a person skilled in the art will appreciate that the residues shown in Table 1 are equivalent. This may also be seen by comparison of the published crystal structures of the BRD-2, BRD-3 and BRD-4 bromodomains, which have all been solved. See Nakamura et al. (J. Biol. Chem. 2007, 282, 4193-4201) for a description of the BRD-2 D1 bromodomain structure, and also protein crystallographic databank entries for BRD-2 D1 (1x0j, 2cvq, 2drv, 2dvs), BRD-2 D2 (2dvv, 2e3k), BRD-3 D1 (2nxb), BRD-3 D2 (2oo1), BRD-4 D1 (2oss) and BRD-4 D2 (2ouo, 2dww).

TABLE 1

| | BRD-2 BD1 | BRD-2 BD2 | BRD-3 BD1 | BRD-3 BD2 | BRD-4 BD1 | BRD-4 BD2 |
|---|---|---|---|---|---|---|
| a | TRP97 | TRP370 | TRP57 | TRP332 | TRP81 | TRP374 |
| b | PRO98 | PRO371 | PRO58 | PRO333 | PRO82 | PRO375 |
| c | TYR113 | TYR386 | TYR73 | TYR348 | TYR97 | TYR390 |
| d | ASN156 | ASN429 | ASN116 | ASN391 | ASN140 | ASN433 |
| e | ASP161 | ASP434 | ASP121 | GLU396 | ASP145 | GLU438 |
| f | ILE162 | VAL435 | ILE122 | VAL397 | ILE146 | VAL439 |
| g | MET165 | MET438 | MET125 | MET400 | MET149 | MET442 |

Thus, in a first aspect the invention provides a process for the identification of compounds with a molecular weight in the range 100 to 750 which inhibit the binding of the first and/or second bromodomains of human BRD-2 to 4 to acetylated lysine residues of their physiological partner proteins which comprises selecting those compounds which are able to:
  a) form a hydrogen bonding interaction in which the compound accepts a hydrogen bond from the sidechain NH2 group of the asparagine residue found at:

| BRD-2 BD1 | BRD-2 BD2 | BRD-3 BD1 | BRD-3 BD2 | BRD-4 BD1 | BRD-4 BD2 |
|---|---|---|---|---|---|
| ASN156 | ASN429 | ASN116 | ASN391 | ASN140 | ASN433 | or
  b) accept a water-mediated hydrogen bond in which the compound accepts a hydrogen bond from a water that is itself hydrogen-bonded to the sidechain hydroxyl of the tyrosine residue found at

| BRD-2 BD1 | BRD-2 BD2 | BRD-3 BD1 | BRD-3 BD2 | BRD-4 BD1 | BRD-4 BD2 |
|---|---|---|---|---|---|
| TYR113 | TYR386 | TYR73 | TYR348 | TYR97 | TYR390 | and
  c) which are also able to form a Van der Waals interaction with a lipophilic binding region of a binding pocket such that one or more heavy atoms of the said compounds lie within a 5 Å range of any of the heavy atoms of the following bromodomain residues which define the binding pocket:

| BRD-2 BD1 | BRD-2 BD2 | BRD-3 BD1 | BRD-3 BD2 | BRD-4 BD1 | BRD-4 BD2 |
|---|---|---|---|---|---|
| TRP97 | TRP370 | TRP57 | TRP332 | TRP81 | TRP374 |
| PRO98 | PRO371 | PRO58 | PRO333 | PRO82 | PRO375 |
| ASP161 | ASP434 | ASP121 | GLU396 | ASP145 | GLU438 |
| ILE162 | VAL435 | ILE122 | VAL397 | ILE146 | VAL439 |
| MET165 | MET438 | MET125 | MET400 | MET149 | MET442 |

In a further aspect of the invention there is provided a process for the identification of compounds with a molecular weight in the range 100 to 750 which inhibit the binding of the first and/or second bromodomains of human BRD-2 to 4 to acetylated lysine residues of their physiological partner proteins which comprises selecting those compounds which are able to:

a) form a hydrogen bonding interaction in which the compound accepts a hydrogen bond from the sidechain NH2 group of the asparagine residue found at:

| BRD-2 BD1 | BRD-2 BD2 | BRD-3 BD1 | BRD-3 BD2 | BRD-4 BD1 | BRD-4 BD2 |
|---|---|---|---|---|---|
| ASN156 | ASN429 | ASN116 | ASN391 | ASN140 | ASN433 | and
b) accept a water-mediated hydrogen bond in which the compound accepts a hydrogen bond from a water that is itself hydrogen-bonded to the sidechain hydroxyl of the tyrosine residue found at

| BRD-2 BD1 | BRD-2 BD2 | BRD-3 BD1 | BRD-3 BD2 | BRD-4 BD1 | BRD-4 BD2 |
|---|---|---|---|---|---|
| TYR113 | TYR386 | TYR73 | TYR348 | TYR97 | TYR390 | and
c) which are also able to form a Van der Waals interaction with a lipophilic binding region of a binding pocket such that one or more heavy atoms of the said compounds lie within a 5 Å range of any of the heavy atoms of the following bromodomain residues which define the binding pocket:

| BRD-2 BD1 | BRD-2 BD2 | BRD-3 BD1 | BRD-3 BD2 | BRD-4 BD1 | BRD-4 BD2 |
|---|---|---|---|---|---|
| TRP97 | TRP370 | TRP57 | TRP332 | TRP81 | TRP374 |
| PRO98 | PRO371 | PRO58 | PRO333 | PRO82 | PRO375 |
| ASP161 | ASP434 | ASP121 | GLU396 | ASP145 | GLU438 |
| ILE162 | VAL435 | ILE122 | VAL397 | ILE146 | VAL439 |
| MET165 | MET438 | MET125 | MET400 | MET149 | MET442 |

In a further aspect of the invention there is provided a process wherein step (c) requires the compounds to be able to form a Van der Waals interaction with a lipophilic binding region of a binding pocket such that one or more heavy atoms of the said compounds lie within 7.5 Å of at least one heavy atom of each of the 3 residues listed for a given bromodomain

| BRD-2 BD1 | BRD-2 BD2 | BRD-3 BD1 | BRD-3 BD2 | BRD-4 BD1 | BRD-4 BD2 |
|---|---|---|---|---|---|
| PRO98 | PRO371 | PRO58 | PRO333 | PRO82 | PRO375 |
| ASP161 | ASP434 | ASP121 | GLU396 | ASP145 | GLU438 |
| ILE162 | VAL435 | ILE122 | VAL397 | ILE146 | VAL439 |

In a yet further aspect of the invention there is provided a process wherein step (a) and/or (b) is performed first to allow identification of a compound fragment, before step (c) is performed to modify the fragment identified from steps (a) and/or (b) to provide a compound with a molecular weight in the range 100 to 750 which inhibit the binding of the first and/or second bromodomains of human BRD-2 to 4 to acetylated lysine residues of their physiological partner proteins. The person skilled in the art will recognise this to be fragment based compound identification and optimisation.

In a further aspect the invention provides a process for the identification of compounds with a molecular weight in the range 100 to 500 which inhibit the binding of the first and/or second bromodomains of human BRD-2 to 4 to acetylated lysine residues of their physiological partner proteins which comprises selecting those compounds which are able to:

a) form a hydrogen bonding interaction in which the compound accepts a hydrogen bond from the sidechain NH2 group of the asparagine residue found at:

| BRD-2 BD1 | BRD-2 BD2 | BRD-3 BD1 | BRD-3 BD2 | BRD-4 BD1 | BRD-4 BD2 |
|---|---|---|---|---|---|
| ASN156 | ASN429 | ASN116 | ASN391 | ASN140 | ASN433 | or
b) accept a water-mediated hydrogen bond in which the compound accepts a hydrogen bond from a water that is itself hydrogen-bonded to the sidechain hydroxyl of the tyrosine residue found at

| BRD-2 BD1 | BRD-2 BD2 | BRD-3 BD1 | BRD-3 BD2 | BRD-4 BD1 | BRD-4 BD2 |
|---|---|---|---|---|---|
| TYR113 | TYR386 | TYR73 | TYR348 | TYR97 | TYR390 | and
c) which are also able to form a Van der Waals interaction with a lipophilic binding region of a binding pocket such that one or more heavy atoms of the said compounds lie within a 5 Å range of any of the heavy atoms of the following bromodomain residues which define the binding pocket:

| BRD-2 BD1 | BRD-2 BD2 | BRD-3 BD1 | BRD-3 BD2 | BRD-4 BD1 | BRD-4 BD2 |
|---|---|---|---|---|---|
| TRP97 | TRP370 | TRP57 | TRP332 | TRP81 | TRP374 |
| PRO98 | PRO371 | PRO58 | PRO333 | PRO82 | PRO375 |
| ASP161 | ASP434 | ASP121 | GLU396 | ASP145 | GLU438 |
| ILE162 | VAL435 | ILE122 | VAL397 | ILE146 | VAL439 |
| MET165 | MET438 | MET125 | MET400 | MET149 | MET442 |

In a further aspect of the invention there is provided a process for the identification of compounds with a molecular weight in the range 100 to 500 which inhibit the binding of the first and/or second bromodomains of human BRD-2 to 4 to acetylated lysine residues of their physiological partner proteins which comprises selecting those compounds which are able to:

a) form a hydrogen bonding interaction in which the compound accepts a hydrogen bond from the sidechain NH2 group of the asparagine residue found at:

| BRD-2 BD1 | BRD-2 BD2 | BRD-3 BD1 | BRD-3 BD2 | BRD-4 BD1 | BRD-4 BD2 |
|---|---|---|---|---|---|
| ASN156 | ASN429 | ASN116 | ASN391 | ASN140 | ASN433 | and
b) accept a water-mediated hydrogen bond in which the compound accepts a hydrogen bond from a water that is itself hydrogen-bonded to the sidechain hydroxyl of the tyrosine residue found at

| BRD-2 BD1 | BRD-2 BD2 | BRD-3 BD1 | BRD-3 BD2 | BRD-4 BD1 | BRD-4 BD2 |
|---|---|---|---|---|---|
| TYR113 | TYR386 | TYR73 | TYR348 | TYR97 | TYR390 | and
c) which are also able to form a Van der Waals interaction with a lipophilic binding region of a binding pocket such that one or more heavy atoms of the said compounds lie within a 5 Å range of any of the heavy atoms of the following bromodomain residues which define the binding pocket:

| BRD-2 BD1 | BRD-2 BD2 | BRD-3 BD1 | BRD-3 BD2 | BRD-4 BD1 | BRD-4 BD2 |
|---|---|---|---|---|---|
| TRP97 | TRP370 | TRP57 | TRP332 | TRP81 | TRP374 |
| PRO98 | PRO371 | PRO58 | PRO333 | PRO82 | PRO375 |
| ASP161 | ASP434 | ASP121 | GLU396 | ASP145 | GLU438 |
| ILE162 | VAL435 | ILE122 | VAL397 | ILE146 | VAL439 |
| MET165 | MET438 | MET125 | MET400 | MET149 | MET442 |

In a further aspect of the invention there is provided a process wherein step (c) requires the compounds to be able to form a Van der Waals interaction with a lipophilic binding region of a binding pocket such that one or more heavy atoms of the said compounds lie within 7.5 Å of at least one heavy atom of each of the 3 residues listed for a given bromodomain

| BRD-2 BD1 | BRD-2 BD2 | BRD-3 BD1 | BRD-3 BD2 | BRD-4 BD1 | BRD-4 BD2 |
|---|---|---|---|---|---|
| PRO98 | PRO371 | PRO58 | PRO333 | PRO82 | PRO375 |
| ASP161 | ASP434 | ASP121 | GLU396 | ASP145 | GLU438 |
| ILE162 | VAL435 | ILE122 | VAL397 | ILE146 | VAL439 |

In a yet further aspect of the invention there is provided a process wherein step (a) and/or (b) is performed first to allow identification of a compound fragment, before step (c) is performed to modify the fragment identified from steps (a) and/or (b) to provide a compound with a molecular weight in the range 100 to 500 which inhibit the binding of the first and/or second bromodomains of human BRD-2 to 4 to acetylated lysine residues of their physiological partner proteins. The person skilled in the art will recognise this to be fragment based compound identification and optimisation.

There are many ways in which compounds that take advantage of the interactions described above may be discovered or designed. In a process known as virtual screening, molecules can be identified from databases of real or virtual compounds. Methods to do this may make use of the protein structure, (e.g. docking), of the 3D ligand structure, (e.g. pharmacophore searching, shape-based or field-based similarity searching), or of the 2D ligand structure (e.g. similarity or substructure searching), or by combinations of these approaches. Similar methods may also be used to design new compounds, either from first principles or by modification of existing active molecules, in a process known as de novo design. A person skilled in the art will be aware of many ways in which such activities can be carried out, including but not limited to those described in review articles, recent examples of which include Muegge & Oloff, Drug Discovery Today: Technologies, 2006, 3, 405-411; Kontoyianni et al. Current Medicinal Chemistry, 2008, 15, 107-116; Seifert & Lang, Mini-Reviews in Medicinal Chemistry, 2007, 63-72; the sections of Comprehensive Medicinal Chemistry II, Vol 4: Computer-Assisted Drug Design, ed. Taylor & Triggle, Elsevier 2007.

The compounds identified using the above-mentioned processes form a further aspect of the invention and are hereinafter referred to as "compounds of the invention".

It will be appreciated that, whilst the compounds of the invention may bind to each of BD1 and 2 of the human BRD-2 to 4 proteins, the kinetics and binding affinity may be different at each of these binding sites.

It will be appreciated that when synthesised the compounds of the invention may exist as a free base or a salt or solvate thereof, for example as a pharmaceutically acceptable salt thereof. The present invention covers compounds of the invention as the free base and as salts thereof, for example as a pharmaceutically acceptable salt thereof. In one embodiment the invention relates to compounds of the invention or a pharmaceutically acceptable salt thereof.

Because of their potential use in medicine, salts of the compounds of the invention are desirably pharmaceutically acceptable. Suitable pharmaceutically acceptable salts can include acid or base addition salts. As used herein, the term 'pharmaceutically acceptable salt' means any pharmaceutically acceptable salt or solvate of a compound of the invention, which upon administration to the recipient is capable of providing (directly or indirectly). For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable base addition salt can be formed by reaction of a compound of the invention with a suitable inorganic or organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

A pharmaceutically acceptable acid addition salt can be formed by reaction of a compound of the invention with a suitable inorganic or organic acid (such as hydrobromic, hydrochloric, sulphuric, nitric, phosphoric, succinc, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of the invention can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Other non-pharmaceutically acceptable salts, e.g. formates, oxalates or trifluoroacetates, may be used, for example in the isolation of the compounds of the invention, and are included within the scope of this invention.

The invention includes within its scope all possible stoichiometric and non-stoichiometric forms of the salts of the compounds of the invention.

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. Solvates of the compounds of the invention are within the scope of the invention.

The invention includes within its scope all possible stoichiometric and non-stoichiometric forms of the solvates of the compounds of the invention.

The invention encompasses all prodrugs, of the compound of the invention, which upon administration to the recipient is capable of providing (directly or indirectly) the compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

The compounds of the invention may be in crystalline or amorphous form. Furthermore, some of the crystalline forms of the compounds of the invention may exist as polymorphs, which are included within the scope of the present invention. Polymorphic forms of compounds of the invention may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Certain compounds of the invention may exist in one of several tautomeric forms. It will be understood that the present invention encompasses all tautomers of the compounds of the invention whether as individual tautomers or as mixtures thereof.

It will be appreciated from the foregoing that included within the scope of the invention are solvates, hydrates, complexes and polymorphic forms of the compounds of the invention and salts thereof.

The compounds of the invention are bromodomain inhibitors, and thus to believed to have potential utility in the treatment of diseases or conditions for which a bromodomain is indicated.

The present invention thus provides a compound of the invention for use in therapy. The compound of the invention can be for use in the treatment of diseases or conditions for which a bromodomain inhibitor indicated.

The present invention thus provides a compound of the invention for use in the treatment of any diseases or conditions for which a bromodomain is indicated.

Also provided is the use of a compound of the invention in the manufacture of a medicament for the treatment of diseases or conditions for which a bromodomain inhibitor is indicated.

Also provided is a method of treating diseases or conditions for which a bromodomain inhibitor is indicated in a subject in need thereof which comprises administering a therapeutically effective amount of compound of the invention or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement, acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus and poxvirus and other DNA viruses.

Bromodomain inhibitors may be useful in the treatment of cancer, including hematological, epithelial including lung, breast and colon carcinomas, midline carcinomas, mesenchymal, hepatic, renal and neurological tumours.

The term "diseases or conditions for which a bromodomain inhibitor is indicated", is intended to include any of or all of the above disease states.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock or endotoxaemia. In another embodiment, the bromodomain inhibitor is indicated for the treatment of acute or chronic pancreatitis. In another embodiment the bromodomain is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, poxvirus infections such as cowpox and smallpox and African swine fever virus. In one particular embodiment a bromodomain inhibitor is indicated for the treatment of Human papilloma virus infections of skin or cervical epithelia.

While it is possible that for use in therapy, a compound of the invention as well as pharmaceutically acceptable salts thereof may be administered as the raw chemical, it is common to present the active ingredient as a pharmaceutical composition.

The present invention therefore provides in a further aspect a pharmaceutical composition comprising a compound of the invention or a pharmaceutically acceptable salt and one or more or pharmaceutically acceptable carriers, diluents and/or excipients. The compounds of the formula (I) and pharmaceutically acceptable salts, are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of the formula (I), or a pharmaceutically acceptable salt thereof, with one or more pharmaceutically acceptable carriers, diluents or excipients. The pharmaceutical composition can be for use in the treatment of any of the conditions described herein.

Since the compounds of the invention are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, as, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Dosage forms for nasal or inhaled administration may conveniently be formulated as aerosols, solutions, suspensions, gels or dry powders.

For compositions suitable and/or adapted for inhaled administration, it is preferred that the compound of the invention is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of the invention or salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose e.g. lactose monohydrate and the compound of the invention or salt thereof. Such compositions can be administered to the patient using a suitable device such as the DISKUS® device, marketed by GlaxoSmithKline which is for example described in GB 2242134 A.

The compounds of the invention thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of the invention calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds the invention can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same.

An effective amount of a salt thereof, may be determined as a proportion of the effective amount of the compound of the invention per se.

The compounds of the invention and may be employed alone or in combination with other therapeutic agents. Combination therapies according to the present invention thus comprise the administration of at least one compound of the invention or a pharmaceutically acceptable salt thereof, and the use of at least one other pharmaceutically active agent. Preferably, combination therapies according to the present invention comprise the administration of at least one compound of the invention or a pharmaceutically acceptable salt thereof, and at least one other pharmaceutically active agent. The compound(s) of the invention and the other pharmaceutically active agent(s) may be administered together in a single pharmaceutical composition or separately and, when administered separately this may occur simultaneously or sequentially in any order. The amounts of the compound(s) of the invention and the other pharmaceutically active agent(s) and the relative timings of administration will be selected in order to achieve the desired combined therapeutic effect. Thus in a further aspect, there is provided a combination comprising a compound of the invention and at least one other pharmaceutically active agent.

Thus in one aspect, the compound and pharmaceutical compositions according to the invention may be used in combination with or include one or more other therapeutic agents, for example selected from antibiotics, anti-virals, glucocorticosteroids, muscarinic antagonists and beta-2 agonists.

It will be appreciated that when the compound of the present invention is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

Background Experimental
LCMS Methods
Method B

LC/MS (Method B) was conducted on an Acquity UPLC BEH C18 column (50 mm×2.1 mm i.d. 1.7 μm packing diameter) at 40 degrees centigrade, eluting with 0.1% v/v solution of Formic Acid in Water (Solvent A) and 0.1% v/v solution of Formic Acid in Acetonitrile (Solvent B) using the following elution gradient 0-1.5 min 3-100% B, 1.5-1.9 min 100% B, 1.9-2.0 min 3% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

Method D

LC/MS (Method D) was conducted on a Supelcosil LCABZ+PLUS column (3 µm, 3.3 cm×4.6 mm ID) eluting with 0.1% HCO$_2$H and 0.01 M ammonium acetate in water (solvent A), and 95% acetonitrile and 0.05% HCO$_2$H in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 mL/minute. The mass spectra (MS) were recorded on a Fisons VG Platform mass spectrometer using electrospray positive ionisation [(ES+ve to give [M+H]$^+$ and [M+NH$_4$]$^+$ molecular ions] or electrospray negative ionisation [(ES–ve to give [M–H]– molecular ion] modes. Analytical data from this apparatus are given with the following format: [M+H]$^+$ or [M–H]$^-$.

Method E

LC/MS (Method E) was conducted on a Chromolith Performance RP 18 column (100×4.6 mm id) eluting with 0.01M ammonium acetate in water (solvent A) and 100% acetonitrile (solvent B), using the following elution gradient 0-4 minutes 0-100% B, 4-5 minutes 100% B at a flow rate of 5 ml/minute. The mass spectra (MS) were recorded on a micromass Platform-LC mass spectrometer using atmospheric pressure chemical positive ionisation [AP+ve to give MH+ molecular ions] or atmospheric pressure chemical negative ionisation [AP–ve to give (M–H)– molecular ions] modes. Analytical data from this apparatus are given with the following format: [M+H]+ or [M–H]–.

Method F

LC/MS (Method F) was conducted on an Sunfire C18 column (30 mm×4.6 mm i.d. 3.5 µm packing diameter) at 30 degrees centigrade, eluting with 0.1% v/v solution of Trifluoroacetic Acid in Water (Solvent A) and 0.1% v/v solution of Trifluoroacetic Acid in Acetonitrile (Solvent B) using the following elution gradient 0-0.1 min 3% B, 0.1-4.2 min 3-100% B, 4.2-4.8 min 100% B, 4.8-4.9 min 100-3% B, 4.9-5.0 min 3% B at a flow rate of 3 ml/min. The UV detection was an averaged signal from wavelength of 210 nm to 350 nm and mass spectra were recorded on a mass spectrometer using positive electrospray ionization. Ionisation data was rounded to the nearest integer.

Compound (I)

(+)-Phenylmethyl (1-methyl-6-phenyl-4H-[1,2,4]triazolo[4,3-a][1,4]benzodiazepin-4-yl)carbamate

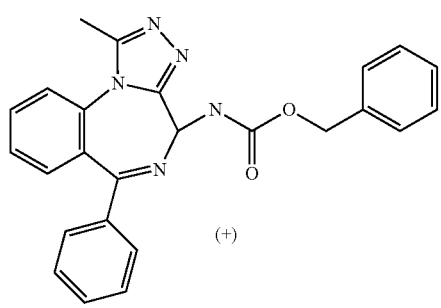 [SMILES: Cc1nnc2n1-c1ccccc1C(c1ccccc1)=NC2NC(=O)OCc1ccccc1]

(+)

Racemic mixture of phenylmethyl (1-methyl-6-phenyl-4H-[1,2,4]triazolo[4,3-a][1,4]benzodiazepin-4-yl)carbamate [prepared according to the procedure described in the J. Med. Chem., (1988, 31(1), 176-181)] was separated by HPLC using a (R,R) whelk-01 column with Hexane/EtOH as the mobile phase. The sample was prepared in a 80/20 mixture EtOH/Hexane (Note: the sample required heating and filtering prior to addition to the column). The system used for preparative separation was as follows: Column: (R,R) Whel-01 51×250 mm column (2 inch columns); mobile phase: 50/50, Hexane/EtOH; Flow rate: 45.0 mL/min; UV wavelength: 254 nm. The title compound eluted at 49 min as the first peak. [α]$_D$=+44.7 c=1.0525 (g/100 mL)/MeOH. The other enantiomer came off at 58 minutes.

Intermediate 1

[1-(1H-1,2,3-benzotriazol-1-yl)ethyl](4-bromophenyl)amine

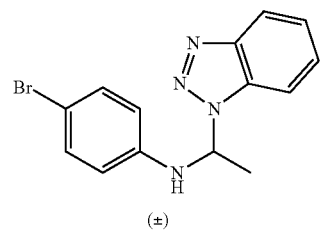

(±)

To a suspension of benzotriazole (139 g, 1.16 mol) in toluene (2 L) in a 3 L, four neck flask under nitrogen atmosphere was added at room temperature a solution of 4-bromoaniline (200 g, 1.16 mol) in toluene (300 mL). Then, via a dropping funnel was added drop wise acetaldehyde (64.7 ml, 1.17 mol) in solution in toluene (200 mL). The reaction mixture becomes progressively homogenous and then gives a precipitate. The resulting mixture is stirred 12 hours under nitrogen atmosphere and then filtered. The precipitate is recrystallised in toluene to afford the title compound as a white solid (304 g, 82%).

1H NMR (300 MHz, CHLOROFORM-d) δ ppm 2.1 (m, 3H) 4.9 (m, 0.66H) 5.15 (m, 0.33H) 6.5-6.9 (m, 3H) 7.2-8.2 (m, 7H)

Intermediate 2

(6-bromo-2-methyl-1,2,3,4-tetrahydro-4-quinolinyl)formamide

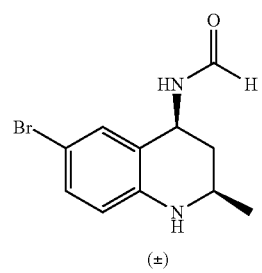

(±)

A 3 L, four neck flask under nitrogen atmosphere was charged with N-vinyl formamide (66.2 g, 0.946 mol) and dry THF (400 mL). BF$_3$Et$_2$O (239 mL, 1.9 mol) were added dropwise at –5° C. to the milky mixture. After 15 minutes Intermediate 1 (150 g, 0.473 mol) in solution in THF (1 L) was added at –5° C. After 2 h, the mixture was slowly and carefully poured in a NaHCO$_3$ saturated solution (5 L). Ethyl acetate (2 L) was added and the mixture was transferred to a separating funnel. The organic layer was separated and was washed 1×200 mL H$_2$O, 1×200 mL brine and dried (Na$_2$SO$_4$). The mixture was filtered and the solids washed 1×50 mL ethyl acetate. The filtrate was concentrated progressively until a precipitate appeared and the mixture cooled in an ice bath during 2 h. The precipitate was filtered through a Buchner funnel, and washed with 2×100 mL i-Pr$_2$O to deliver the title compound as a solid (71 g, 56%).

LC/MS: (Method E), m/z 269 and 271 [M+H]$^+$, Rt=2.29 min; 1H NMR (300 MHz, CHLOROFORM-d) δ ppm 0.98 (d, 3H) 1.24 (q, 1H) 2.04 (ddd, 1H) 3.33 (m, 1H) 5.17 (m, 1H) 5.45 (m, 1H) 6.15 (d, 1H) 6.88 (dd, 1H) 7.00 (d, 1H) 8.11 (s, 1H)

Intermediate 3

[1-acetyl-6-bromo-2-methyl-1,2,3,4-tetrahydro-4-quinolinyl]formamide

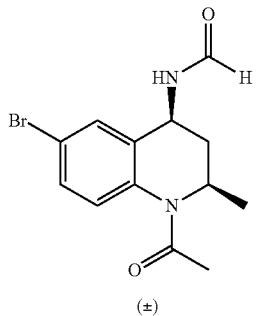 [SMILES: CC(=O)N1c2ccc(Br)cc2[C@@H](NC=O)C[C@H]1C]

(±)

Acetyl chloride (21 mL, 0.29 mol) is added dropwise at 0° C. to a solution of Intermediate 2 (71 g, 0.26 mol) in a mixture of DCM (1 L) and pyridine (350 mL). After stirring 2 hours at 0° C. the mixture is poured into a mixture of crushed ice (2 kg) and concentrated HCl (450 mL). The product is extracted with DCM (1 L) washed with brine and dried over Na$_2$SO$_4$. Concentration under vacuo afforded the expected product as an off white solid (82 g, 100%).

1H NMR (300 MHz, CHLOROFORM-d) δ ppm 0.98 (d, 3H) 1.15 (m, 1H) 1.95 (s, 3H) 2.4 (m, 1H) 4.7 (m, 1H) 4.85 (m, 1H) 5.8 (br d, 1H) 6.85 (d, 1H) 7.15 (s, 1H) 7.25 (d, 1H) 8.2 (s, 1H)

Intermediate 4

Methyl 4-[1-acetyl-4-(formylamino)-2-methyl-1,2,3,4-tetrahydro-6-quinolinyl]benzoate

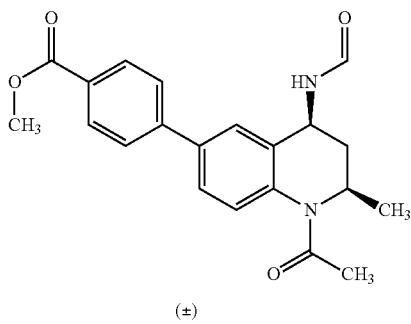 [SMILES: COC(=O)c1ccc(-c2ccc3c(c2)[C@@H](NC=O)C[C@@H](C)N3C(C)=O)cc1]

(±)

To a suspension of Intermediate 3 (1-acetyl-6-bromo-2-methyl-1,2,3,4-tetrahydro-4-quinolinyl)formamide (62.24 g) in DME (600 ml) was added palladium tetrakis (11.56 g) at room temperature. After 10 min of stirring, were added {4-[(methyloxy)carbonyl]phenyl}boronic acid (54 g) and a 2N solution of Na$_2$CO$_3$ (300 mL) and the mixture was stirred heated to reflux for 16 h. The mixture was concentrated under reduced pressure. After addition of 200 ml of DCM to the residue, the product precipitated, it was filtered and washed with water (3*100 mL). To remove the rest of the water, the solid was washed with isopropyl ether (100 ml), the solid was then added to 220 ml of warm isopropyl ether and the resulting mixture was left in the sonicator. The solid was filtered off and dried to afford the title compound as a beige solid (64.7 g)

LCMS (Method E) Rt 2.58 MH+ 367

Intermediate 5

Methyl 4-(1-acetyl-4-amino-2-methyl-1,2,3,4-tetrahydro-6-quinolinyl)benzoate

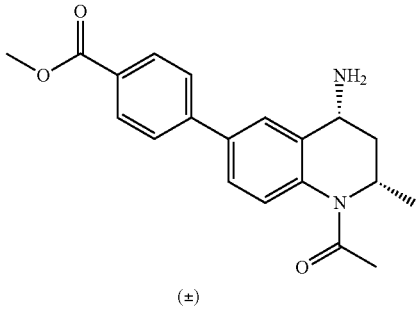

(±)

A suspension of Intermediate 4 (20.0 g) in methanol (400 mL) was refluxed, then treated with HCl 6N (18 mL). The resulting mixture was refluxed for 2 h. The suspension was filtered off on whatman and the filtrate was concentrated until dryness. Acetone (70 mL) was added to the residue, the solid was filtered off and dried. The resulting salt in ethyl acetate (300 mL) was treated with NaOH 1N (100 ml). Aqueous and organic layers were separated. Aqueous layer was extracted with CH$_2$Cl$_2$/MeOH 9:1 (300 mL). The organic layers were combined, dried and concentrated until dryness to give the title compound as a white solid (13.83 g).

LCMS (Method E) Rt 2.51 MH+ 339

Intermediate 6

(2S,3S)-2,3-bis[(phenylcarbonyl)oxy]butanedioic acid-methyl 4-(1-acetyl-4-amino-2-methyl-1,2,3,4-tetrahydro-6-quinolinyl)benzoate (1:2)

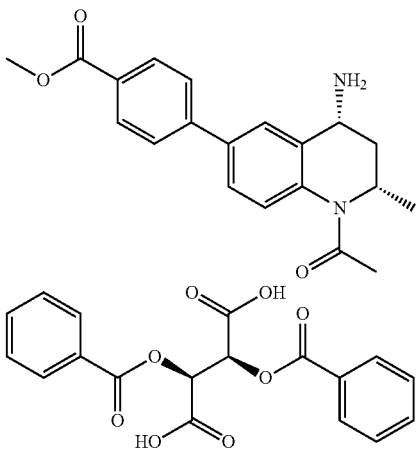

A mixture of the racemic amine Intermediate 5 (185 g,) in EtOH (600 mL) and L-(+)-lactic acid (20% in water, 450 mL) was heated to reflux during 30 minutes. After concentration under reduced pressure hexane (300 mL) was added to the residue and the resulting mixture heated to reflux 10 min. The mixture was allowed to settle and the hexane phase was discarded. The remaining paste was taken up with Et$_2$O (300 mL), heated to reflux during 10 minutes and allowed to settle. The Et$_2$O phase was discarded and the resulting paste once again was treated with hexane (200 mL), heated to reflux and allowed to settle. The hexane phase was discarded and EtOAc (2.3 L) was added to the remaining paste. The mixture was heated to reflux and allowed to stand at room temperature for 16 hours. The precipitate was filtered and washed with EtOAc (200 mL). The filtrate was made basic with addition of Na$_2$CO$_3$ and the resulting free amino was extracted with EtOAc (3×1000 mL), washed with water, dried over Na$_2$SO$_4$ and concentrated under reduced pressure. The resulting free amino (95 g) in solution in THF (950 mL) was treated with L(−)-dibenzoyltartaric acid (50.3 g, 0.14 mol) and heated to reflux 30 minutes. The resulting precipitate was allowed to stand at room temperature during 16 hours and then was filtered and washed with THF (200 ml). An HPLC monitoring of a neutralised aliquot indicated a 95.6% ee of the expected amine enantiomer. Recrystallisation of the tartaric salt in EtOH (1 L) afforded the title compound (95 g) as a single diastereomer salt.

mp: 196° C. 1H NMR (300 MHz, DMSO-d6) δ ppm 0.95 (d, 3H) 1.15 (m, 1H) 2.05 (s, 3H) 2.55 (m, 1H) 3.85 (s, 3H) 4.0 (m, 1H) 4.55 (m, 1H) 5.7 (s, 1H, CH tartaric) 7.4 (m, 3H) 7.6 (m, 2H) 7.85 (m, 3H), 7.95 (m, 4H).

Intermediate 7

Methyl 4-[(2S,4R)-1-acetyl-4-amino-2-methyl-1,2,3,4-tetrahydro-6-quinolinyl]benzoate

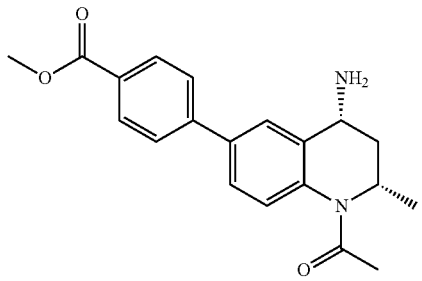

A mixture of Intermediate 6 (121 g) in DCM (3 L) was made basic with addition of an aqueous solution of Na$_2$CO$_3$. The resulting free amine was extracted with DCM (2 L) washed with water and dried over Na$_2$SO$_4$ to deliver the title compound as an off white solid (79 g).

1H NMR (300 MHz, CHLOROFORM-d) δ ppm 1.15 (m, 4H) 1.7 (m, 2H) 2.15 (s, 3H) 2.6 (m, 1H) 3.8 (dd, 1H), 3.95 (s, 3H) 4.85 (m, 1H) 7.2 (d, 1H) 7.55 (d, 1H) 7.7 (d, 2H), 7.8 (s, 1H) 8.1 (d, 2H) [α]$_D$=+333.8 (c=0.985 g/cl, EtOH).

The title compound eluted at 18.57 min by HPLC as the second peak using a CHIRACEL OD (250×4.6 mm 10 μm) column with hexane/ethanol 80/20 as the mobile phase. A 1 ml/mn flow rate was applied and 10 μL of sample prepared with the dilution of 1 mg of the title compound in 1 ml of eluent was injected. Detection of the compound was carried out with both 210 and 254 nM UV wavelengths. The other enantiomer came off at 12.8 min.

Intermediate 8

Methyl 4-{(2S,4R)-1-acetyl-4-[(4-chlorophenyl)amino]-2-methyl-1,2,3,4-tetrahydro-6-quinolinyl}benzoate

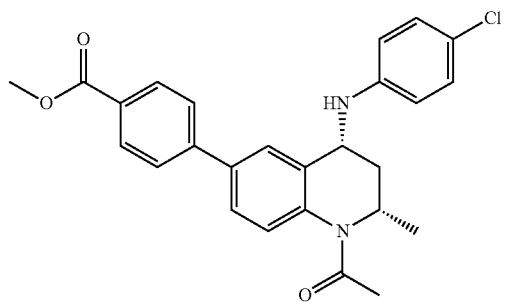 [SMILES: COC(=O)c1ccc(-c2ccc3c(c2)[C@H](Nc2ccc(Cl)cc2)C[C@H](C)N3C(C)=O)cc1]

To a flask charged with the Intermediate 7 (800 mg, 2.4 mmol) in toluene (20 mL) was added 4-chlorobromobenzene (501 mg, 2.6 mmol), Pd$_2$(dba)$_3$ (87 mg, 0.09 mmol), NaO$^t$Bu (319 mg, 3.3 mmol) and 2'-(dicyclohexylphosphanyl)-N,N-dimethyl-2-biphenylamine (74 mg, 0.19 mmol). The resulting mixture was stirred to 80° C. during 16 hours and 3 additional hours at reflux. The mixture was poured into water and was made acidic upon addition of 1N HCl. Extraction was carried out with EtOAc (2×75 ml) and the organic layers were washed with water and dried over Na$_2$SO4. After filtration, concentration under reduced pressure and purification by column chromatography eluting with C$_6$H$_{12}$/EtOAc:80/20 the title compound was obtained as a white solid (350 mg).

1H NMR (300 MHz, CHLOROFORM-d) δ ppm 1.2 (d, 3H) 1.35 (m, 1H) 2.25 (s, 3H) 2.7 (m, 1H) 3.95 (s, 3H), 4.25 (m, 1H) 4.95 (m, 1H) 6.6 (d, 2H) 7.15 (d, 2H) 7.25 (s, 1H) 7.55 (m, 4H), 8.1 (d, 2H) LC/MS (Method D): m/z 449 [M+H]$^+$ and 447 [M−H]$^−$ Rt=3.67 min. [α]$_D$=+326 (c=0.98 g/cl, EtOH)

The title compound eluted at 22.58 min by HPLC as the second peak using a CHIRACEL OD (250×4.6 mm 10 μm) column with hexane/ethanol 90/10 as the mobile phase. A 1 ml/mn flow rate was applied and 10 μL of sample prepared with the dilution of 1 mg of the title compound in 1 ml of eluent was injected. Detection of the compound was carried out with both 210 and 254 nM UV wavelengths. The other enantiomer came off at 15.46 min.

Compound (II)

4-{(2S,4R)-1-acetyl-4-[(4-chlorophenyl)amino]-2-methyl-1,2,3,4-tetrahydro-6-quinolinyl}benzoic acid

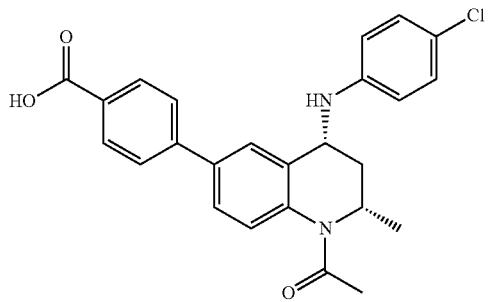 [SMILES: CC(=O)N1c2ccc(-c3ccc(C(=O)O)cc3)cc2[C@H](Nc2ccc(Cl)cc2)C[C@@H]1C]

A solution of Intermediate 8 (320 mg, 0.73 mmol) in EtOH (10 ml) and 1N NaOH (1.5 ml, 1.5 mmol) was heated to reflux. After 1 hour a tlc monitoring indicated the completion of the reaction. The crude mixture was evaporated to dryness and the residue taken up in water (10 mL). Acidification of the mixture at pH=3 was carried out by addition of a 1N HCl solution. The organic materials were extracted with EtOAc (3×25 mL) and the organic phase combined and washed with brine and dried over $Na_2SO_4$. After concentration under vacuo the residue was taken up in a DCM/hexane mixture to give a red solid after filtration. The compound was recrystallised in EtOAC, filtered and washed with i-$Pr_2O$. The resulting white powder was solubilised in MeOH/$H_2O$, concentrated to dryness and taken up with $H_2O$. Finally filtration of the precipitate afforded the title compound as a white powder (147 mg), mp: 275° C.

HRMS calculated for $C_{25}H_{23}N_2O_3Cl$ (M−H)$^-$ 433.1319. Found: 433.1299. Rt: 2.21 min. 1H NMR (300 MHz, CHLOROFORM-d) δ ppm 1.2 (d, 3H) 1.35 (m, 1H) 2.3 (s, 3H) 2.7 (m, 1H) 4.25 (dd, 1H) 4.95 (m, 1H) 6.65 (d, 2H) 7.15 (d, 2H) 7.25 (s, 1H) 7.55 (m, 4H), 8.15 (d, 2H)

$[\alpha]_D$=+395 (c=0.96 g/cl, EtOH) measured at the EtOAc recrystallisation stage.

The title compound eluted at 4.51 min by HPLC as the first peak using a Chiralpak IA (250×4.6 mm 5 μm) column with tert-butyl methyl oxide (MTBE) +0.1% TFA/Ethanol: 90/10 as the mobile phase. A 1 ml/mn flow rate was applied and 10 μL of sample prepared with the dilution of 1 mg of the title compound in 1 ml of eluent was injected. Detection of the compound was carried out with both 210 and 254 nM UV wavelengths. The other enantiomer came off at 5.92 min.

Compound (III)

1-Acetyl-2-methyl-1,2,3,4-tetrahydroquinoline

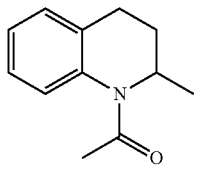

2-Methyl-1,2,3,4-tetrahydroquinoline (216 mg, 1.469 mmol, available from TCI), was measured into a reaction test tube and acetic anhydride (0.139 ml, 1.469 mmol) was added and left to stir overnight. LCMS analysis showed the reaction had gone to completion. The crude product was purified by MDAP to give the desired compound (677 mg)

LCMS (Method B). RT 0.93, MH+ 190

Intermediate 9

1-methylethyl (2E)-2-butenoylcarbamate

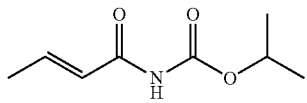

Isopropyl carbamate (30 g, 291 mmol, available from TCI) was charged to a 3 L Lara vessel and dry Tetrahydrofuran (THF) (150 ml) added. (2E)-2-butenoyl chloride (31.2 ml, 326 mmol, available from Aldrich) was added under Nitrogen and the jacket cooled to −30° C. When the solution temperature reached −17° C. 1M Lithium tert-butoxide (655 ml, 655 mmol) was added by peristaltic pump over 2 hours, keeping the reaction temperature between −10° C. and −18° C. Once the addition was complete the mixture was complete the mixture was stirred for 30 mins and brought to 0° C. Diethyl ether (450 ml) and 1M HCl (375 ml) were added and the mixture brought to 20° C. with vigourous stirring. The stirring was stopped, the layers allowed to separate and the aqueous layer run off. Brine (375 ml) was added and the mixture stirred vigourously. The stirring was stopped, the layers allowed to separate and the aqueous layer run off. The organic layer was dried (magnesium sulfate), filtered and evaporated to a brown oil (60 g). The mixture was loaded on to a 40+M Biotage silica column and eluted with DCM:ethyl acetate (1:1 to 0:1, 10 CV). The product containing fractions were evaporated to dryness and loaded on to a 1500 g Redisep Isco silica column and eluted with a gradient of 0 to 40% ethyl acetate in cyclohexane. The clean, product containing fractions were evaporated to an off white solid (15.41 g). LCMS (Method C): Rt=0.68, MH+=172

Intermediate 10

(R-BINAP)ditriflatebis(acetonitrile)palladium(II)

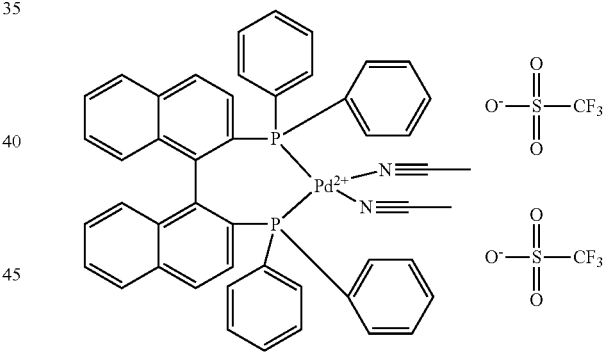

R-(+)-BINAP (6.08 g, 9.76 mmol, available from Avocado) was stirred in Dichloromethane (DCM) (626 ml) and dichlorobis(acetonitrile)palladium (II) (2.5 g, 9.64 mmol, available from Aldrich) added. The mixture was stirred under Nitrogen for 30 mins, the suspension had not become a solution and more DCM (100 ml) was added. The mixture was stirred for a further 30 mins and Silver triflate (5.00 g, 19.47 mmol, available from Aldrich) dissolved in Acetonitrile (250 ml) was added. The mixture changed from an orange cloudy suspension to a yellow suspension. The mixture was stirred for 1 hour, filtered through celite and evaporated to an orange solid. The residue was dried under vacuum (at approximately 14 mbar) at room temperature over the weekend to give the desired product (10.69 g).

1H NMR (400 MHz, MeCN-d3) δ ppm 2.0 (s, 6H), 6.7 (d, 2H), 6.9 (br m, 4H), 7.1 (br t, 2H), 7.2 (t, 2H), 7.5-7.9 (m, 22H)

Intermediate 11

(3S)-3-(phenylamino)butanenitrile

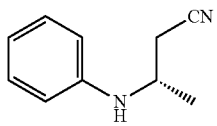

(3S)-3-aminobutanenitrile (8.6 g, 102 mmol, may be prepared as described in PCT Int. Appl., 2005100321), bromobenzene (16.16 ml, 153 mmol) and cesium carbonate (50.0 g, 153 mmol) were combined in Toluene (100 ml) under nitrogen were stirred for 45 mins. Phenylboronic acid (0.187 g, 1.534 mmol, Aldrich), palladium(II) acetate (0.188 g, 0.837 mmol, available from Aldrich) and 2-dicyclohexylphosphino-2'-(N,N-dimethylamino)biphenyl (0.443 g, 1.125 mmol, available from Aldrich) were combined in Tetrahydrofuran (THF) (6.67 ml) under nitrogen and stirred for 45 mins. The THF solution was added to the toluene solution and the reaction heated to 80° C. overnight. The reaction mixture was cooled and partitioned between EtOAc (500 ml) and water (300 ml). The aqueous layer was reextracted with EtOAc (200 ml). The combined organic layers were washed with water and brine (500 ml each) and then dried with Na2SO4, filtered and concentrated to yield an orange oil. The crude product was taken up in the minimum of DCM, applied to a 330 g Companion XL column and eluted with 5% Ethyl Acetate in cyclohexane for 1 CV then 5-30% Ethyl Acetate over 12 CV then held at 30% for 3 CV; UV collection; 450 ml fractions. The product was isolated as an off-white solid (11.3526 g).

LCMS (Method B): Rt=0.87, MH+=161

Intermediate 12

(3S)-3-[(4-bromophenyl)amino]butanenitrile

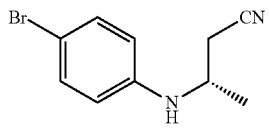

(3S)-3-(phenylamino)butanenitrile (for a preparation see Intermediate 11)(11.3526 g, 70.9 mmol) was taken up in N,N-Dimethylformamide (DMF) (200 mL) under nitrogen and cooled in an ice-bath. NBS (12.61 g, 70.9 mmol) was added and the reaction stirred. After 20 mins, the reaction was partitioned between EtOAc (1000 ml) and water (500 ml). The organic layer was washed with 2M NaOH×2, water and brine (500 ml each) and then dried with Na2SO4, filtered and concentrated to yield the product as a cream solid (17.3 g). LCMS (Method B): Rt=1.05, MH+=239

Intermediate 13

(3S)-3-[(4-bromophenyl)amino]butanamide

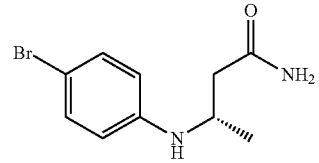

(3S)-3-[(4-bromophenyl)amino]butanenitrile (for a preparation see Intermediate 12)(17.3 g, 72.4 mmol) was taken up in Toluene (500 ml) and H2SO4 (19.28 ml, 362 mmol) added. The biphasic mixture was stirred at 60° C. After two hours, only a small amount of SM remained by LCMS so the reaction was diluted with water (500 ml) and the phases separated. The aqueous phase was basified with 10N NaOH and extracted with EtOAc (2×750 ml). The combined organics were dried with Na2SO4, filtered and concentrated to yield the product as a cream solid (17.5 g). LCMS (Method B): Rt=0.77, MH+=257

Intermediate 14

1-methylethyl {(3S)-3-[(4-bromophenyl)amino] butanoyl}carbamate

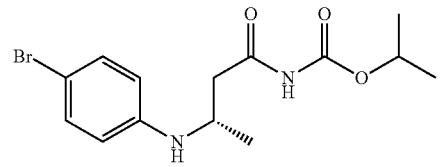 [SMILES: CC(C)OC(=O)NC(=O)C[C@H](C)Nc1ccc(Br)cc1]

(3S)-3-[(4-bromophenyl)amino]butanamide (for a preparation see Intermediate 13, 24.9 g, 97 mmol) was taken up in Ethyl acetate (850 mL) and cooled to <-9° C. (internal). Isopropyl chloroformate (116 mL, 116 mmol, Aldrich) was added followed by slow addition of Lithium tert-butoxide (18.61 g, 232 mmol) in Tetrahydrofuran (THF) (232 mL) keeping the temperature below 0° C. The reaction was stirred for 30 mins then checked by LCMS which showed a complete reaction. The mixture was partitioned between EtOAc (1000 ml) and 2N HCl (2000 ml). The organic layer was washed with brine (2000 ml) and then dried with Na2SO4, filtered and concentrated to yield the product as a brown oil (17.9 g)

LCMS (Method B): Rt=1.09, MH+=343

Alternative Method 1-methylethyl (2E)-2-butenoylcarbamate (Intermediate 9, 9.38 g, 54.8 mmol) was stirred in Toluene (281 ml) under nitrogen and (R-BINAP)ditriflatebis(acetonitrile)palladium (II) (Intermediate 10, 3.35 g, 3.01 mmol) added. The catalyst formed a gummy ball, the solution turned to an opaque yellow mixture and was stirred for 20 mins. 4-bromoaniline (14.14 g, 82 mmol) was added, the solution turned a clear light brown and the gummy catalyst dissolved further. The mixture was stirred overnight, Similarly a second batch of 1-methylethyl (2E)-2-butenoylcarbamate (Intermediate 9, 8.51 g, 49.7 mmol) was stirred in Toluene (255 ml) under nitrogen and (R-BINAP) ditriflatebis(acetonitrile)palladium(II) (3.04 g, 2.73 mmol) added. The catalyst formed a gummy ball, the solution turned to an opaque yellow mixture and was stirred for 20 mins. 4-bromoaniline (12.83 g, 74.6 mmol) was added, the solution turned a clear light brown and the gummy catalyst dissolved further. The mixture was stirred overnight. The two reaction mixtures were combined and loaded on to a 1.5 kg Isco silica Redisep column. The column was eluted with DCM:MeOH (0%->0.5%, 19 CV). The clean, product containing fractions were evaporated to a pale brown oil. The mixture was dried in a vaccum oven overnight at 40° C. to give a white solid (24.2 g, 67% overall).

LCMS (Method C): Rt=0.91, MH+=343. ee=92%.

Intermediate 15

1-methylethyl [(2S,4R)-6-bromo-2-methyl-1,2,3,4-tetrahydro-4-quinolinyl]carbamate

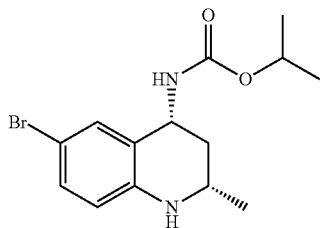 [SMILES: CC(C)OC(=O)N[C@@H]1C[C@H](C)Nc2ccc(Br)cc21]

1-methylethyl {(3S)-3-[(4-bromophenyl)amino]butanoyl}carbamate (for a preparation see Intermediate 14) (17.9 g, 52.2 mmol) was taken up in Ethanol (150 mL) and cooled to below −10° C. (internal) in a CO2/acetone bath. NaBH4 (1.381 g, 36.5 mmol) was added followed by Magnesium Chloride hexahydrate (11.35 g, 55.8 mmol) in Water (25 mL) keeping the temperature below −5° C. The mixture was allowed to stir at <0° C. for 1 hr then warmed to RT and stirred for an hour. The resulting thick suspension was poured into a mixture of citric acid (25.05 g, 130 mmol), HCl (205 mL, 205 mmol) and Dichloromethane (DCM) (205 mL). The biphasic mixture was stirred at RT for 1 hr. LCMS showed no SM remained so the organic layer was extracted and dried with Na2SO4, filtered and concentrated to yield the product as a light brown solid (14.1 g). LCMS (Method B): Rt=1.13, MH+=327

Intermediate 16

1-methylethyl [(2S,4R)-1-acetyl-6-bromo-2-methyl-1,2,3,4-tetrahydro-4-quinolinyl]carbamate

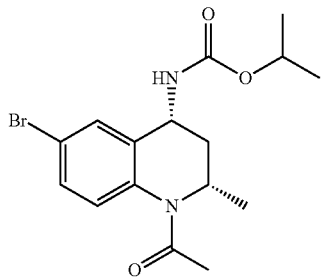 [SMILES: CC(=O)N1c2ccc(Br)cc2[C@H](NC(=O)OC(C)C)C[C@@H]1C]

1-methylethyl [(2S,4R)-6-bromo-2-methyl-1,2,3,4-tetrahydro-4-quinolinyl]carbamate (for a preparation see Intermediate 15)(14.1 g, 43.1 mmol) was taken up in Dichloromethane (DCM) (400 mL) under nitrogen at RT. Pyridine (10.46 mL, 129 mmol) then Acetyl chloride (4.60 mL, 64.6 mmol) were added and the reaction stirred overnight. LCMS showed a complete reaction so it was partitioned between EtOAc (2000 ml) and sat. NaHCO3 (800 ml). The organic layer was extracted and washed with water and brine (1500 ml each) and then dried with Na2SO4, filtered and concentrated to yield a purple solid. The crude product was taken up in the minimum of DCM and applied to a 330 g Companion XL column and eluted with a gradient of 12-63% Ethyl Acetate in cyclohexane. Product containing fractions were collected as an off-white solid (12.37 g).

LCMS (Method B): Rt=1.03, MH+=369 [alpha]D=+281.1025° (T=20.7° C., 10 mm cell, c=0.508 g/100 ml, ethanol).

Intermediate 17

1-methylethyl [(2S,4R)-1-acetyl-6-(4-formylphenyl)-2-methyl-1,2,3,4-tetrahydro-4-quinolinyl]carbamate

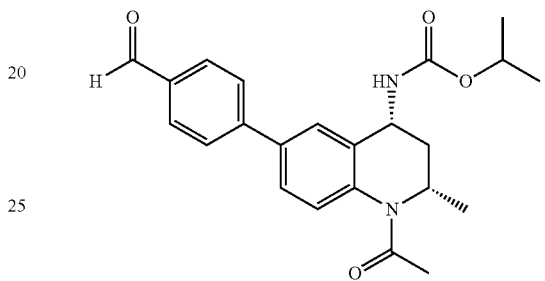

1-methylethyl [(2S,4R)-1-acetyl-6-bromo-2-methyl-1,2,3,4-tetrahydro-4-quinolinyl]carbamate (for a preparation see Intermediate 16)(1 g, 2.71 mmol), (4-formylphenyl)boronic acid (0.487 g, 3.25 mmol, available from Aldrich), Pd(Ph3P)4, (0.156 g, 0.135 mmol) and potassium carbonate (0.487 g, 3.52 mmol) were combined in dry ethanol (7 ml) and dry toluene (7.00 ml) and the reaction mixture was de-gassed for 10 mins. The reaction mixture was heated at 85° C. overnight. The reaction mixture was allowed to cool to r.t. and concentrated. The crude reaction mixture was partitioned between water (15 ml) and ethyl acetate (5 ml) and stirred at r.t. for 30 mins. A light grey solid precipitated out and was filtered off, washed with water (5 ml) and dried in a vacuum oven to give 854 mg of grey solid. LCMS (Method B): Rt=1.00, MH+=395

Compound (IV)

1-methylethyl ((2S,4R)-1-acetyl-2-methyl-6-{4-[(methylamino)methyl]pheny}-1,2,3,4-tetrahydro-4-quinolinyl)carbamate

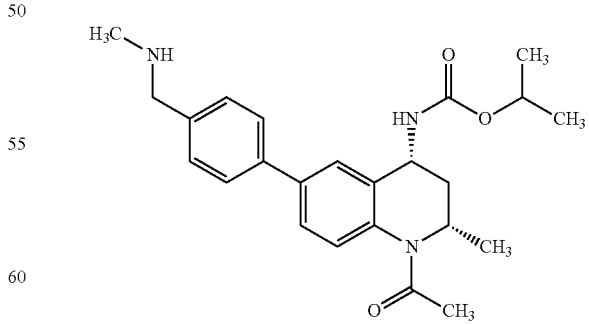

1-methylethyl [(2S,4R)-1-acetyl-6-(4-formylphenyl)-2-methyl-1,2,3,4-tetrahydro-4-quinolinyl]carbamate (for a preparation see Intermediate 17)(100 mg, 0.254 mmol) was dissolved in Methanol (3 mL) and 2M methylamine in THF (0.254 mL, 0.507 mmol) was added. The yellow solution was stirred under nitrogen at room temperature for 135 minutes at which point sodium borohydride (15.35 mg, 0.406 mmol) was added. The reaction was stirred for 1 h then left sitting overnight. The reaction was quenched with sat. aqueous sodium bicarbonate solution (1 mL) and EtOAc (8 mL) was added. A white solid was filtered off (bond elut reservoir) and found to be the desired product (34 mg). The filtrate was partitioned and the organic layer dried. Concentration of the organic layer gave 67 mg of a colourless residue which was applied to a silica 12+S Biotage column and purified eluting with a gradient of 1-5% methanolic ammonia in DCM. Concentration of the product containing fractions gave another batch of the desired product (52 mg).

LCMS (Method C): Rt 0.71, MH+=410 1H NMR (CHLOROFORM-d, 600 MHz): δ (ppm) 7.55 (d, J=8.1 Hz, 2H), 7.49 (d, J=7.9 Hz, 1H), 7.45 (br. s., 1H), 7.41 (d, J=7.9 Hz, 2H), 7.18 (d, J=7.3 Hz, 1H), 4.52-5.08 (m, 4H), 3.81 (s, 2H), 2.62 (ddd, J=12.5, 8.3, 4.5 Hz, 1H), 2.50 (s, 3H), 2.17 (s, 3H), 1.21-1.37 (m, 7H), 1.18 (d, J=6.4 Hz, 3H)

Reference compound A:
2-methyl-6-(methyloxy)-4H-3,1-benzoxazin-4-one

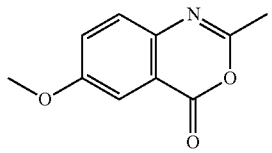

A solution of 5-methoxyanthranilic acid (Lancaster) (41.8 g, 0.25 mol) was refluxed in acetic anhydride (230 mL) for 3.5 h before being concentrated under reduced pressure. The crude compound was then concentrated twice in the presence of toluene before being filtered and washed twice with ether to yield to the title compound (33.7 g, 71% yield) as a brown solid; LC/MS (Method D): m/z 192 [M+H]$^+$, Rt 1.69 min.

Reference compound B: [2-amino-5-(methyloxy)phenyl](4-chlorophenyl)methanone

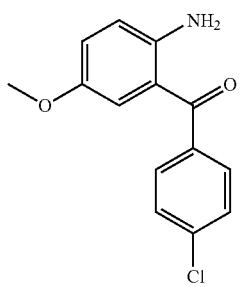 [SMILES: COc1ccc(N)c(C(=O)c2ccc(Cl)cc2)c1]

To a solution of 2-methyl-6-(methyloxy)-4H-3,1-benzoxazin-4-one (for a preparation see Reference compound A) (40.0 g, 0.21 mol) in a toluene/ether (2/1) mixture (760 mL) at 0° C. was added dropwise a solution of 4-chlorophenylmagnesium bromide (170 mL, 1M in Et$_2$O, 0.17 mol). The reaction mixture was allowed to warm to room temperature and stirred for 1 h before being quenched with 1N HCl (200 mL). The aqueous layer was extracted with EtOAc (3×150 mL) and the combined organics were washed with brine (100 mL), dried over Na$_2$SO$_4$, filtered and concentrated under reduced pressure. The crude compound was then dissolved in EtOH (400 mL) and 6N HCl (160 mL) was added. The reaction mixture was refluxed for 2 h before being concentrated to one-third in volume. The resulting solid was filtered and washed twice with ether before being suspended in EtOAc and neutralised with 1N NaOH. The aqueous layer was extracted with EtOAc (3×150 mL) and the combined organics were washed with brine (150 mL), dried over Na$_2$SO$_4$, filtered and concentrated under reduced pressure. The title compound was obtained as a yellow solid (39 g, 88% yield); LC/MS (Method D): m/z 262 [M+H]+, Rt 2.57 min.

Reference Compound C: Methyl N$^1$-[2-[(4-chlorophenyl)carbonyl]-4-(methyloxy)phenyl]-N$^2$-{[(9H-fluoren-9-ylmethyl)oxy]carbonyl}-L-α-asparaginate

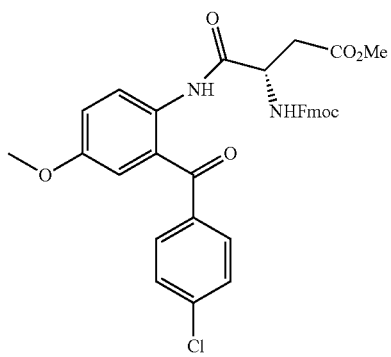

Methyl N-{[(9H-fluoren-9-ylmethyl)oxy]carbonyl}-L-α-aspartyl chloride (Int. J. Peptide Protein Res. 1992, 40, 13-18) (93 g, 0.24 mol) was dissolved in CHCl$_3$ (270 mL) and [2-amino-5-(methyloxy)phenyl](4-chlorophenyl)methanone (53 g, 0.2 mol) (for a preparation see Reference compound B) was added. The resulting mixture was stirred at 60° C. for 1 h before being cooled and concentrated at 60% in volume. Ether was added at 0° C. and the resulting precipitate was filtered and discarded. The filtrate was concentrated under reduced pressure and used without further purification.

Reference compound D: Methyl [(3S)-5-(4-chlorophenyl)-7-(methyloxy)-2-oxo-2,3-dihydro-1H-1,4-benzodiazepin-3-yl]acetate

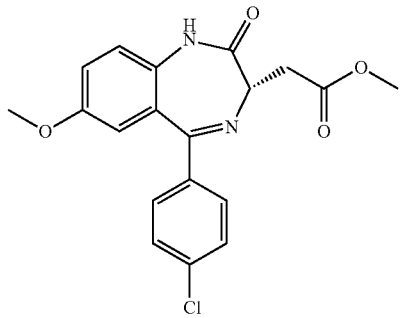

To a solution of methyl N1-[2-[(4-chlorophenyl)carbonyl]-4-(methyloxy)phenyl]-N2-{[(9H-fluoren-9-ylmethyl)oxy]carbonyl}-L-α-asparaginate (for a preparation see Reference compound C) (assumed 0.2 mol) in DCM (500 mL) was added Et$_3$N (500 mL, 3.65 mol) and the resulting mixture was refluxed for 24 h before being concentrated. The resulting crude amine was dissolved in 1,2-DCE (1.5 L) and AcOH (104 mL, 1.8 mol) was added carefully. The reaction mixture was then stirred at 60° C. for 2 h before being concentrated in vacuo and dissolved in DCM. The organic layer was washed with 1N HCl and the aqueous layer was extracted with DCM (×3). The combined organic layers were washed twice with water, and brine, dried over Na$_2$SO$_4$, filtered and concentrated under reduced pressure. The crude solid was recrystallised in MeCN leading to the title compound (51 g) as a pale yellow solid. The filtrate could be concentrated and recrystallised in MeCN to give to another 10 g of the desired product R$_f$=0.34 (DCM/MeOH: 95/5).

HRMS (M+H)$^+$ calculated for C$_{19}$H$_{18}$$^{35}$ClN$_2$O$_4$ 373.0955. Found 373.0957.

Reference compound E: Methyl [(3S)-5-(4-chlorophenyl)-7-(methyloxy)-2-thioxo-2,3-dihydro-1H-1,4-benzodiazepin-3-yl]acetate

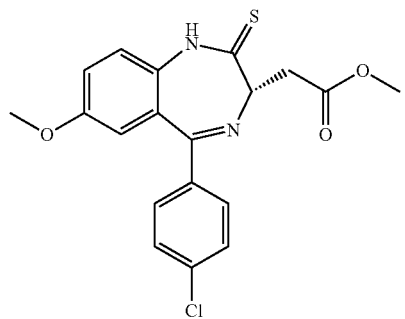

A suspension of P$_4$S$_{10}$ (36.1 g, 81.1 mmol) and Na$_2$CO$_3$ (8.6 g, 81.1 mmol) in 1,2-DCE (700 mL) at room temperature was stirred for 2 h before methyl [(3S)-5-(4-chlorophenyl)-7-(methyloxy)-2-oxo-2,3-dihydro-1H-1,4-benzodiazepin-3-yl]acetate (for a preparation see Reference compound D) (16.8 g, 45.1 mmol) was added. The resulting mixture was stirred at 70° C. for 2 h before being cooled and filtered. The solid was washed twice with DCM and the filtrate washed with sat. NaHCO$_3$ and brine. The organic layer was dried over Na$_2$SO$_4$, filtered and concentrated under reduced pressure. The crude product was purified by flash-chromatography on silica gel (DCM/MeOH: 99/1) to afford the title compound (17.2 g, 98% yield) as a yellowish solid. LC/MS (Method D): m/z 389 [M($^{35}$Cl)+H]$^+$, Rt 2.64 min HRMS (M+H)$^+$ calculated for C$_{19}$H$_{18}$$^{35}$ClN$_2$O$_3$S 389.0727. Found 389.0714.

Reference compound F: Methyl [(3S)-2-[(1Z)-2-acetylhydrazino]-5-(4-chlorophenyl)-7-(methyloxy)-3H-1,4-benzodiazepin-3-yl]acetate

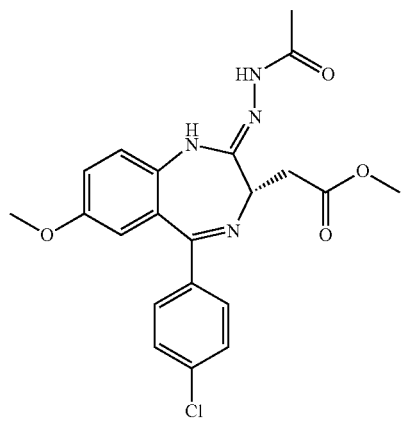

To a suspension of methyl [(3S)-5-(4-chlorophenyl)-7-(methyloxy)-2-thioxo-2,3-dihydro-1H-1,4-benzodiazepin-3-yl]acetate (for a preparation see Reference compound E (9.0 g, 23.2 mmol) in THF (300 mL) at 0° C. was added hydrazine monohydrate (3.4 mL, 69.6 mmol) dropwise. The reaction mixture was stirred for 5 h between 5° C. and 15° C. before being cooled at 0° C. Et$_3$N (9.7 mL, 69.6 mmol) was then added slowly and acetyl chloride (7.95 mL, 69.6 mmol) was added dropwise. The mixture was then allowed to warm to room temperature for 16 h before being concentrated under reduced pressure. The crude product was dissolved in DCM and washed with water. The organic layer was dried over Na$_2$SO$_4$, filtered and concentrated in vacuo to give the crude title compound (9.7 g, 98% yield) which was used without further purification. R$_f$=0.49 (DCM/MeOH: 90/10).

Reference compound G: Methyl [(4S)-6-(4-chlorophenyl)-1-methyl-8-(methyloxy)-4H-[1,2,4]triazolo[4,3-a][1,4]benzodiazepin-4-yl]acetate

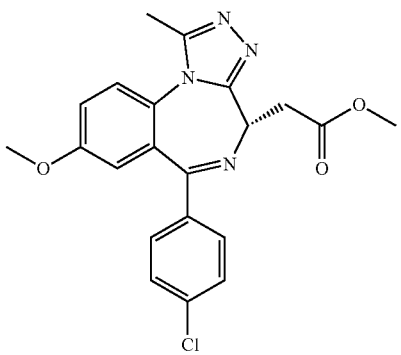

The crude methyl [(3S)-2-[(1Z)-2-acetylhydrazino]-5-(4-chlorophenyl)-7-(methyloxy)-3H-1,4-benzodiazepin-3-yl] acetate (for a preparation see Reference compound F) (assumed 9.7 g) was suspended in THF (100 ml) and AcOH (60 mL) was added at room temperature. The reaction mixture was stirred at this temperature for 2 days before being concentrated under reduced pressure. The crude solid was triturated in i-Pr$_2$O and filtered to give the title compound (8.7 g, 91% over 3 steps) as an off-white solid.

HRMS (M+H)$^+$ calculated for C$_{21}$H$_{20}$ClN$_4$O$_3$ 411.1229. Found 411.1245.

Reference compound H: [(4S)-6-(4-Chlorophenyl)-1-methyl-8-(methyloxy)-4H-[1,2,4]triazolo[4,3-a][1,4]benzodiazepin-4-yl]acetic acid

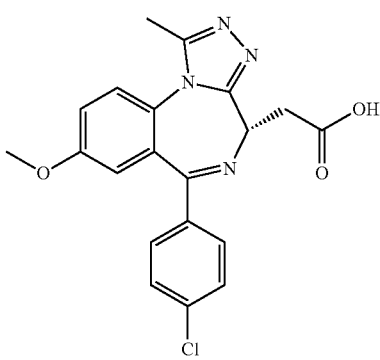 [SMILES: COc1ccc2c(c1)C(c1ccc(Cl)cc1)=N[C@@H](CC(=O)O)c1nnc(C)n1-2]

To a solution of Methyl [(4S)-6-(4-chlorophenyl)-1-methyl-8-(methyloxy)-4H-[1,2,4]triazolo[4,3-a][1,4]benzodiazepin-4-yl]acetate (for a preparation see Reference compound G) (7.4 g, 18.1 mmol) in THF (130 mL) at room temperature was added 1N NaOH (36.2 mL, 36.2 mmol). The reaction mixture was stirred at this temperature for 5 h before being quenched with 1N HCl (36.2 mL) and concentrated in vacuo. Water is then added and the aqueous layer was extracted with DCM (×3) and the combined organic layers were dried over Na$_2$SO$_4$, filtered and concentrated under reduced pressure to give the title compound (7 g, 98% yield) as a pale yellow solid.

Reference compound I: 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate

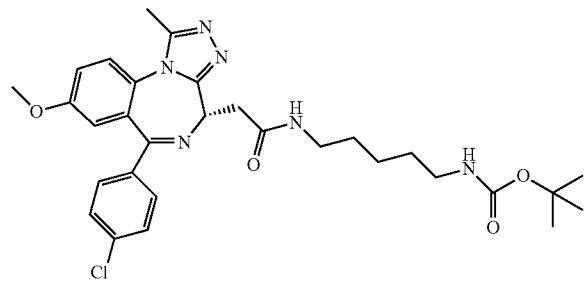 [SMILES: COc1ccc2c(c1)C(c1ccc(Cl)cc1)=N[C@@H](CC(=O)NCCCCCNC(=O)OC(C)(C)C)c1nnc(C)n1-2]

A mixture of [(4S)-6-(4-chlorophenyl)-1-methyl-8-(methyloxy)-4H-[1,2,4]triazolo[4,3-a][1,4]benzodiazepin-4-yl]acetic acid (for a preparation see Reference compound H) (1.0 g, 2.5 mmol), HATU (1.9 g, 5 mmol) and DIPEA (0.88 ml, 5 mmol) was stirred for 80 minutes at room temperature, to this was added 1,1-dimethylethyl (4-aminobutyl)carbamate (1.05 ml, 5.0 mmol, available from Aldrich). The reaction mixture was stirred at room temperature for 2 h before it was concentrated. The residue was taken up in dichloromethane and washed with 1N HCl. The aqueous layer was extracted with dichloromethane twice. Organic layer was washed with 1N sodium hydroxide, followed by a saturated solution of sodium chloride, dried over sodium sulphate and concentrated. The residue was purified by flash-chromatography on silica using dichloromethane/methanol 95/5 to give the title compound as a yellow solid (1.2 g). LC/MS (Method D): rt=3.04 min.

Reference compound J: N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate

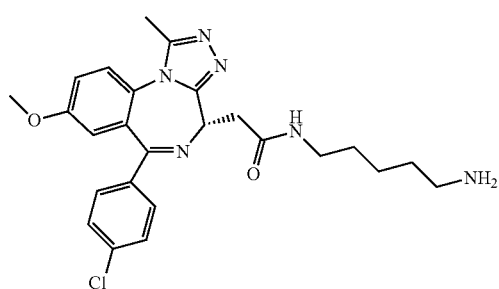 [SMILES: COc1ccc2c(c1)C(c1ccc(Cl)cc1)=N[C@@H](CC(=O)NCCCCCN)c1nnc(C)n1-2]

To a solution of 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate (for a preparation see Reference compound I) (0.2 g, 0.34 mmol) in dichloromethane (3 ml) was added trifluoroacetic acid (0.053 ml, 0.68 mmol) dropwise at 0° C. The reaction mixture was stirred for 3 h from 0° C. to room temperature. The reaction mixture was concentrated to dryness to afford the title compound as a hygroscopic yellow oil (200 mg)

LC/MS (Method D): rt=2.33 min. HRMS (M+H)$^+$ calculated for C$_{25}$H$_{29}$ClN$_6$O$_2$ 481.2119. Found 481.2162.

Reference compound K: Mixture of 5- and 6-isomers of Alexa Fluor 488-N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide

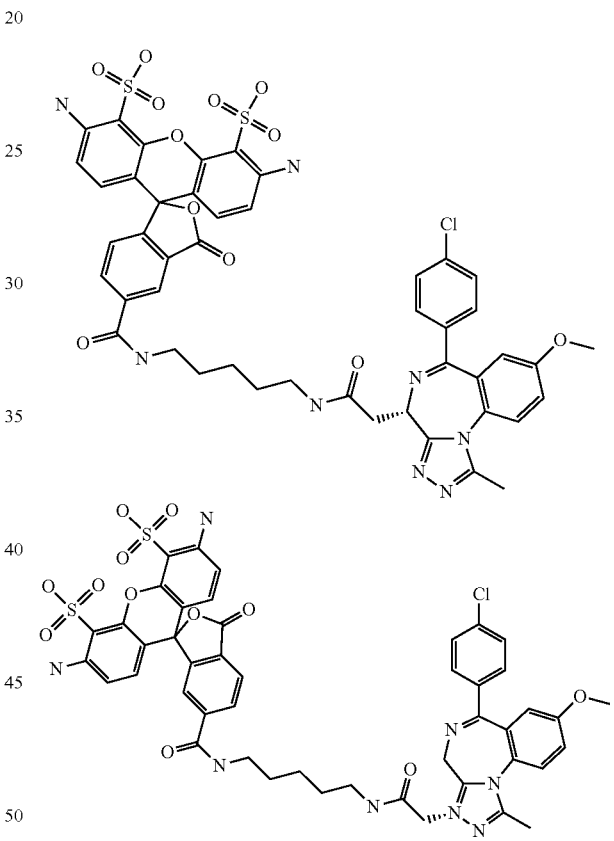

N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate (for a preparation see Reference compound J)(7.65 mg, 0.013 mmol) was dissolved in N,N-Dimethylformamide (DMF) (300 µl) and added to Alexa Fluor 488 carboxylic acid succinimidyl ester (5 mg, 7.77 µmol, mixture of 5 and 6 isomers, available from Invitrogen, product number A-20100) in an Eppendorf centrifuge tube. Hunig's base (7.0 µl, 0.040 mmol) was added and the mixture vortex mixed overnight. After 18 h the reaction mixture was evaporated to dryness and the residue redissolved in DMSO/water (50%, <1 ml total), applied to a preparative Phenomenex Jupiter C18 column and eluted with a gradient of 95% A: 5% B to 100% B (A=0.1% trifluoroacetic acid in water, B=0.1% TFA/90% acetonitrile/

10% water) at a flow rate of 10 ml/min over 150 minutes. Impure fractions were combined and re-purified using the same system. Fractions were combined and evaporated to yield the title product (2.8 mg) as a mixture of the 2 regioisomers shown.

LC/MS (Method F): MH+=999, rt=1.88 min.

Biological Test Methods

Fluorescence Anisotropy Binding Assay

The binding of Compounds (I) to (IV) to Bromodomains BRD-2, BRD-3 and BRD-4 was assessed using a Fluorescence Anisotropy Binding Assay.

The Bromodomain protein, fluorescent ligand (Reference compound K see above) and a variable concentration of test compound are incubated together to reach thermodynamic equilibrium under conditions such that in the absence of test compound the fluorescent ligand is significantly (>50%) bound and in the presence of a sufficient concentration of a potent inhibitor the anisotropy of the unbound fluorescent ligand is measurably different from the bound value.

All data was normalized to the mean of 16 high and 16 low control wells on each plate. A four parameter curve fit of the following form was then applied:

$$y = a + ((b-a)/(1+(10^x/10^c)^d))$$

Where 'a' is the minimum, 'b' is the Hill slope, 'c' is the $pIC_{50}$ and 'd' is the maximum.

Recombinant Human Bromodomains (BRD-2 (1-473), BRD-3 (1-435) and BRD-4 (1-477)) were expressed in *E. coli* cells (in pET15b vector) with a six-His tag at the N-terminal. The His-tagged Bromodomain was extracted from *E. coli* cells using 0.1 mg/ml lysozyme and sonication. The Bromodomain was then purified by affinity chromatography on a HisTRAP HP column, eluting with a linear 10-500 mM Imidazole gradient, over 20 Cv. Further purification was completed by Superdex 200 prep grade size exclusion column. Purified protein was stored at −80 C in 20 mM HEPES pH 7.5 and 100 mM NaCl.

Protocol for Bromodomain BRD-2: All components were dissolved in buffer composition of 50 mM HEPES pH7.4, 150 mm NaCl and 0.5 mM CHAPS with final concentrations of BRD-2, 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Protocol for Bromodomain BRD-3: All components were dissolved in buffer of composition 50 mM HEPES pH7.4, 150 mm NaCl and 0.5 mM CHAPS with final concentrations of BRD-3 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Protocol for Bromodomain BRD-4: All components were dissolved in buffer of composition 50 mM HEPES pH7.4, 150 mm NaCl and 0.5 mM CHAPS with final concentrations of BRD-4 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Compounds (I), (II) and (IV) had a $pIC_{50} \geq 6.0$ in each of the BRD-2, BRD-3 and BRD-4 assays described above.

Compound (III) had a $pIC_{50} \leq 4.3$ in each of the BRD-2, BRD-3 and BRD-4 assays described above.

All publications, including but not limited to patents and patent applications, cited in this specification are herein incorporated by reference as if each individual publication were specifically and individually indicated to be incorporated by reference herein as though fully set forth.

SEQUENCE LISTING

```
<160> NUMBER OF SEQ ID NOS: 6

<210> SEQ ID NO 1
<211> LENGTH: 138
<212> TYPE: PRT
<213> ORGANISM: Homo Sapiens

<400> SEQUENCE: 1

Pro Ala Asn Pro Pro Pro Glu Val Ser Asn Pro Lys Lys Pro Gly
1               5                   10                  15

Arg Val Thr Asn Gln Leu Gln Tyr Leu His Lys Val Val Met Lys Ala
            20                  25                  30

Leu Trp Lys His Gln Phe Ala Trp Pro Phe Arg Gln Pro Val Asp Ala
        35                  40                  45

Val Lys Leu Gly Leu Pro Asp Tyr His Lys Ile Ile Lys Gln Pro Met
    50                  55                  60

Asp Met Gly Thr Ile Lys Arg Arg Leu Glu Asn Asn Tyr Tyr Trp Ala
65                  70                  75                  80

Ala Ser Glu Cys Met Gln Asp Phe Asn Thr Met Phe Thr Asn Cys Tyr
```

```
            85                  90                  95
Ile Tyr Asn Lys Pro Thr Asp Asp Ile Val Leu Met Ala Gln Thr Leu
            100                 105                 110

Glu Lys Ile Phe Leu Gln Lys Val Ala Ser Met Pro Gln Glu Glu Gln
            115                 120                 125

Glu Leu Val Val Thr Ile Pro Lys Asn Ser
            130                 135

<210> SEQ ID NO 2
<211> LENGTH: 141
<212> TYPE: PRT
<213> ORGANISM: Homo Sapiens

<400> SEQUENCE: 2

Pro Val Asn Pro Pro Pro Glu Val Ser Asn Pro Ser Lys Pro Gly
 1               5                   10                  15

Arg Lys Thr Asn Gln Leu Gln Tyr Met Gln Asn Val Val Lys Thr
            20                  25                  30

Leu Trp Lys His Gln Phe Ala Trp Pro Phe Tyr Gln Pro Val Asp Ala
            35                  40                  45

Ile Lys Leu Asn Leu Pro Asp Tyr His Lys Ile Ile Lys Asn Pro Met
 50                  55                  60

Asp Met Gly Thr Ile Lys Lys Arg Leu Glu Asn Asn Tyr Tyr Trp Ser
65                  70                  75                  80

Ala Ser Glu Cys Met Gln Asp Phe Asn Thr Met Phe Thr Asn Cys Tyr
            85                  90                  95

Ile Tyr Asn Lys Pro Thr Asp Asp Ile Val Leu Met Ala Gln Ala Leu
            100                 105                 110

Glu Lys Ile Phe Leu Gln Lys Val Ala Gln Met Pro Gln Glu Glu Val
            115                 120                 125

Glu Leu Leu Pro Pro Ala Pro Lys Gly Lys Gly Arg Lys
            130                 135                 140

<210> SEQ ID NO 3
<211> LENGTH: 143
<212> TYPE: PRT
<213> ORGANISM: Homo Sapiens

<400> SEQUENCE: 3

Ser Thr Asn Pro Pro Pro Glu Thr Ser Asn Pro Asn Lys Pro Lys
 1               5                   10                  15

Arg Gln Thr Asn Gln Leu Gln Tyr Leu Leu Arg Val Val Leu Lys Thr
            20                  25                  30

Leu Trp Lys His Gln Phe Ala Trp Pro Phe Gln Gln Pro Val Asp Ala
            35                  40                  45

Val Lys Leu Asn Leu Pro Asp Tyr Tyr Lys Ile Ile Lys Thr Pro Met
 50                  55                  60

Asp Met Gly Thr Ile Lys Lys Arg Leu Glu Asn Asn Tyr Tyr Trp Asn
65                  70                  75                  80

Ala Gln Glu Cys Ile Gln Asp Phe Asn Thr Met Phe Thr Asn Cys Tyr
            85                  90                  95

Ile Tyr Asn Lys Pro Gly Asp Asp Ile Val Leu Met Ala Glu Ala Leu
            100                 105                 110

Glu Lys Leu Phe Leu Gln Lys Ile Asn Glu Leu Pro Thr Glu Glu Thr
            115                 120                 125

Glu Ile Met Ile Val Gln Ala Lys Gly Arg Gly Arg Gly Arg Lys
```

```
            130                 135                 140

<210> SEQ ID NO 4
<211> LENGTH: 126
<212> TYPE: PRT
<213> ORGANISM: Homo Sapiens

<400> SEQUENCE: 4

Gln Ser Ser Lys Lys Gly Lys Leu Ser Glu Gln Leu Lys His Cys Asn
  1               5                  10                  15

Gly Ile Leu Lys Glu Leu Leu Ser Lys Lys His Ala Ala Tyr Ala Trp
             20                  25                  30

Pro Phe Tyr Lys Pro Val Asp Ala Ser Ala Leu Gly Leu His Asp Tyr
         35                  40                  45

His Asp Ile Ile Lys His Pro Met Asp Leu Ser Thr Val Lys Arg Lys
     50                  55                  60

Met Glu Asn Arg Asp Tyr Arg Asp Ala Gln Glu Phe Ala Ala Asp Val
 65                  70                  75                  80

Arg Leu Met Phe Ser Asn Cys Tyr Lys Tyr Asn Pro Pro Asp His Asp
                 85                  90                  95

Val Val Ala Met Ala Arg Lys Leu Gln Asp Val Phe Glu Phe Arg Tyr
            100                 105                 110

Ala Lys Met Pro Asp Glu Pro Leu Glu Pro Gly Pro Leu Pro
            115                 120                 125

<210> SEQ ID NO 5
<211> LENGTH: 126
<212> TYPE: PRT
<213> ORGANISM: Homo Sapiens

<400> SEQUENCE: 5

His Ala Gly Lys Lys Gly Lys Leu Ser Glu His Leu Arg Tyr Cys Asp
  1               5                  10                  15

Ser Ile Leu Arg Glu Met Leu Ser Lys Lys His Ala Ala Tyr Ala Trp
             20                  25                  30

Pro Phe Tyr Lys Pro Val Asp Ala Glu Ala Leu Glu Leu His Asp Tyr
         35                  40                  45

His Asp Ile Ile Lys His Pro Met Asp Leu Ser Thr Val Lys Arg Lys
     50                  55                  60

Met Asp Gly Arg Glu Tyr Pro Asp Ala Gln Gly Phe Ala Ala Asp Val
 65                  70                  75                  80

Arg Leu Met Phe Ser Asn Cys Tyr Lys Tyr Asn Pro Pro Asp His Glu
                 85                  90                  95

Val Val Ala Met Ala Arg Lys Leu Gln Asp Val Phe Glu Met Arg Phe
            100                 105                 110

Ala Lys Met Pro Asp Glu Pro Val Glu Ala Pro Ala Leu Pro
            115                 120                 125

<210> SEQ ID NO 6
<211> LENGTH: 126
<212> TYPE: PRT
<213> ORGANISM: Homo Sapiens

<400> SEQUENCE: 6

Ala Pro Glu Lys Ser Ser Lys Val Ser Glu Gln Leu Lys Cys Cys Ser
  1               5                  10                  15

Gly Ile Leu Lys Glu Met Phe Ala Lys Lys His Ala Ala Tyr Ala Trp
             20                  25                  30
```

| | | | | | | | | | | | | | |
|---|---|---|---|---|---|---|---|---|---|---|---|---|---|
| Pro | Phe | Tyr<br>35 | Lys | Pro | Val | Asp<br>40 | Val | Glu | Ala | Leu | Gly | Leu<br>45 | His | Asp | Tyr |
| Cys | Asp<br>50 | Ile | Ile | Lys | His | Pro<br>55 | Met | Asp | Met | Ser | Thr<br>60 | Ile | Lys | Ser | Lys |
| Leu<br>65 | Glu | Ala | Arg | Glu | Tyr<br>70 | Arg | Asp | Ala | Gln | Glu<br>75 | Phe | Gly | Ala | Asp | Val<br>80 |
| Arg | Leu | Met | Phe | Ser<br>85 | Asn | Cys | Tyr | Lys | Tyr<br>90 | Asn | Pro | Pro | Asp | His<br>95 | Glu |
| Val | Val | Ala | Met<br>100 | Ala | Arg | Lys | Leu | Gln<br>105 | Asp | Val | Phe | Glu | Met<br>110 | Arg | Phe |
| Ala | Lys | Met<br>115 | Pro | Asp | Glu | Pro | Glu<br>120 | Glu | Pro | Val | Val | Ala<br>125 | Val | | |

The invention claimed is:

1. A process for the identification of a compound which inhibits the binding of the first bromodomain of each of human BRD-2, BRD-3, and BRD-4 to acetylated lysine residues of their physiological partner proteins which process comprises the steps of:
 1) selecting compounds with a molecular weight in the range 100 to 750 Da; and
 2) determining which of those selected compounds is an interacting compound, wherein an interacting compound will:
  a) form a hydrogen bonding interaction in which the compound accepts a hydrogen bond from the side chain $NH_2$ group of the asparagine residue found at: ASN156 of BRD-2 BD1, or ASN116 of BRD-3 BD1, or ASN140 of BRD-4 BD1 and
  b) form a Van der Waals interaction with a lipophilic binding region of a binding pocket such that one or more heavy atoms of the said compounds lie within a 7.5 Å range of at least one heavy atom of each of the 3 residues of the first bromodomain wherein said bromodomain residues are selected from the group consisting of:
  PRO98, ASP161, and ILE162 of BRD-2 BD1;
  PRO58, ASP121, and ILE122 of BRD-3 BD1; and
  PRO82, ASP145, and ILE146 of BRD-4 BD1 and
 3) testing the ability of the interacting compound to inhibit the binding of the first bromodomain to a fluorescent ligand in a fluorescent anisotropy binding assay; wherein the fluorescent ligand is a compound having the structure

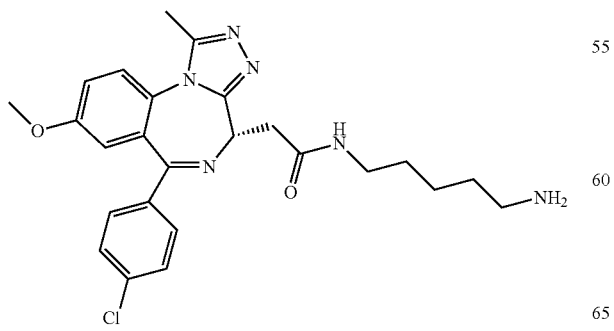

conjugated with a fluorescent label at the terminal amino group (—$NH_2$) of the compound; and wherein the interacting compound which is able to inhibit the binding of the first bromodomain to the fluorescent ligand in the fluorescent anisotropy binding assay is identified as the compound which inhibits the binding of the first bromodomain of each of human BRD-2, BRD-3 and BRD-4 to the acetylated lysine residues of their physiological partner proteins.

2. A process for the identification of a compound which inhibits the binding of the first bromodomain of each of human BRD-2, BRD-3, and BRD-4 to acetylated lysine residues of their physiological partner proteins which process comprises the steps of:
 1) selecting compounds with a molecular weight in the range 100 to 750 Da;
 2) determining which of those selected compounds is an interacting compound, wherein an interacting compound will:
  a) form a hydrogen bonding interaction in which the compound accepts a hydrogen bond from the sidechain $NH_2$ group of the asparagine residue found at: ASN156 of BRD-2 BD1, or ASN116 of BRD-3 BD1, or ASN140 of BRD-4 BD1 and
  b) accept a water-mediated hydrogen bond in which the compound accepts a hydrogen bond from a water that is itself hydrogen-bonded to the sidechain hydroxyl of the tyrosine residue found at the TYR113 of BRD-2 BD1, or TYR73 of BRD-3 BD1, or TYR97 of BRD-4 BD1 and
  c) form a Van der Waals interaction with a lipophilic binding region of a binding pocket such that one or more heavy atoms of the said compounds lie within a 7.5 Å range of at least one heavy atom of each of the 3 residues of the first bromodomain wherein said first bromodomain residues are selected from the group consisting of:
  PRO98, ASP161, and ILE162 of BRD-2 BD1;
  PRO58, ASP121, and ILE122 of BRD-3 BD1; and
  PRO82, ASP145, and ILE146 of BRD-4 BD1; and
 3) testing the ability of the interacting compound to inhibit the binding of the first bromodomain to a fluorescent ligand in a fluorescent anisotropy binding assay; wherein the fluorescent ligand is a compound having the structure

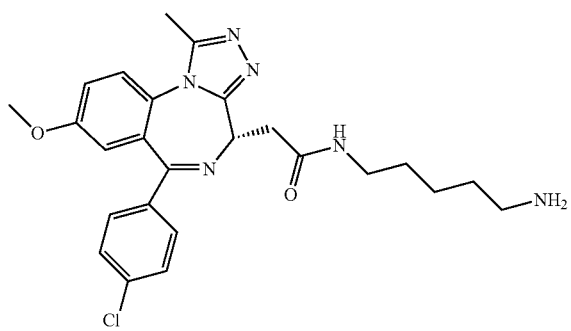 [SMILES: COc1ccc2c(c1)C(c1ccc(Cl)cc1)=N[C@@H](CC(=O)NCCCCCN)c1nnc(C)n1-2]
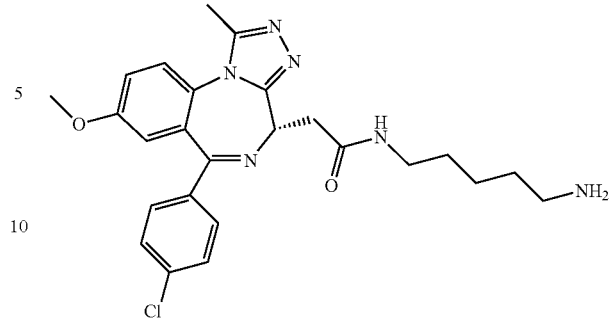

conjugated with a fluorescent label at the terminal amino group (—NH$_2$) of the compound; and wherein the interacting compound which is able to inhibit the binding of the first bromodomain to the fluorescent ligand in the fluorescent anisotropy binding assay is identified as the compound which inhibits the binding of the first bromodomain of each of human BRD-2, BRD-3 and BRD-4 to the acetylated lysine residues of their physiological partner proteins.

3. A process according to claim 1 wherein said molecular weight is in the range 100 to 500 Da.

4. A process according to claim 2 wherein said molecular weight is in the range 100 to 500 Da.

5. A process for the identification of a compound which inhibits the binding of the first bromodomain of each of human BRD-2, BRD-3, and BRD-4 to acetylated lysine residues of their physiological partner proteins which process comprises the steps of:

1) selecting compounds with a molecular weight in the range 100 to 750 Da; and 2) determining which of those selected compounds is an interacting compound, wherein an interacting compound will:

a) form a hydrogen bonding interaction in which the compound accepts a hydrogen bond from the sidechain NH$_2$ group of the asparagine residue found at: ASN156 of BRD-2 BD1, or ASN116 of BRD-3 BD1, or ASN140 of BRD-4 BD1 and b) form a Van der Waals interaction with a lipophilic binding region of a binding pocket such that one or more heavy atoms of the said compounds lie within a 7.5 Å range of at least one heavy atom of each of the 3 residues of the first bromodomain wherein said bromodomain residues are selected from the group consisting of:

PRO98, ASP161, and ILE162 of BRD-2 BD1;

PRO58, ASP121, and ILE122 of BRD-3 BD1; and

PRO82, ASP145, and ILE146 of BRD-4 BD1; and 3) testing the ability of the interacting compound to inhibit the binding of the first bromodomain to a fluorescent ligand in a fluorescent anisotropy binding assay, wherein the fluorescent ligand is a compound having the structure conjugated with a fluorescent label at the terminal amino group (—NH$_2$) of the compound wherein the first bromodomain is comprised in a human bromodomain protein that comprises a histidine tag; and wherein the interacting compound which is able to inhibit the binding of the first bromodomain to the fluorescent ligand in the fluorescent anisotropy binding assay is identified as the compound which inhibits the binding of the first bromodomain of each of human BRD-2, BRD-3 and BRD-4 to the acetylated lysine residues of their physiological partner proteins.

6. A process according to claim 5 wherein said molecular weight is in the range 100 to 500 Da.

7. A process for the identification of a compound which inhibits the binding of the first bromodomain of each of human BRD-2, BRD-3, and BRD-4 to acetylated lysine residues of their physiological partner proteins which process comprises the steps of:

1) selecting compounds with a molecular weight in the range 100 to 750 Da;

2) determining which of those selected compounds is an interacting compound, wherein an interacting compound will:

a) form a hydrogen bonding interaction in which the compound accepts a hydrogen bond from the sidechain NH$_2$ group of the asparagine residue found at: ASN156 of BRD-2 BD1, or ASN116 of BRD-3 BD1, or ASN140 of BRD-4 BD1 and b) accept a water-mediated hydrogen bond in which the compound accepts a hydrogen bond from a water that is itself hydrogen-bonded to the sidechain hydroxyl of the tyrosine residue found at the TYR113 of BRD-2 BD1, or TYR73 of BRD-3 BD1, or TYR97 of BRD-4 BD1 and c) form a Van der Waals interaction with a lipophilic binding region of a binding pocket such that one or more heavy atoms of the said compounds lie within a 7.5 Å range of at least one heavy atom of each of the 3 residues of the first bromodomain wherein said bromodomain residues are selected from the group consisting of:

PRO98, ASP161, and ILE162 of BRD-2 BD1;

PRO58, ASP121, and ILE122 of BRD-3 BD1; and

PRO82, ASP145, and ILE146 of BRD-4 BD1; and 3) testing the ability of the interacting compound to inhibit the binding of the first bromodomain to a fluorescent ligand in a fluorescent anisotropy binding assay, wherein the fluorescent ligand is a compound having the structure

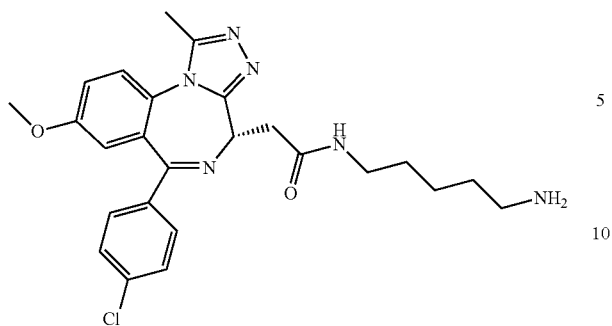

conjugated with a fluorescent label at the terminal amino group (—NH₂) of the compound, wherein the first bromodomain is comprised in a human bromodomain protein that comprises a histidine tag; and wherein the interacting compound which is able to inhibit the binding of the first bromodomain to the fluorescent ligand in the fluorescent anisotropy binding assay is identified as the compound which inhibits the binding of the first bromodomain of each of human BRD-2, BRD-3 and BRD-4 to the acetylated lysine residues of their physiological partner proteins.

8. A process according to claim 7 wherein said molecular weight is in the range 100 to 500 Da.

* * * * *